(12) United States Patent
Zentes et al.

(10) Patent No.: US 8,439,950 B2
(45) Date of Patent: May 14, 2013

(54) IMPLANT TO BE LOCATED BETWEEN ADJACENT SPINOUS PROCESSES

(75) Inventors: Klaus P. Zentes, Quierschied (DE); Uwe Siedler, Alzzenau (DE)

(73) Assignee: Taurus GmbH & Co. KG, Cologne (DE)

( * ) Notice: Subject to any disclaimer, the term of this patent is extended or adjusted under 35 U.S.C. 154(b) by 556 days.

(21) Appl. No.: 12/263,890

(22) Filed: Nov. 3, 2008

(65) Prior Publication Data

US 2009/0149886 A1 Jun. 11, 2009

Related U.S. Application Data

(60) Provisional application No. 60/990,080, filed on Nov. 26, 2007.

(30) Foreign Application Priority Data

Nov. 2, 2007 (DE) .......................... 10 2007 052 799

(51) Int. Cl.
*A61B 17/70* (2006.01)

(52) U.S. Cl.
USPC ......................................... 606/248; 606/249

(58) Field of Classification Search .......... 606/246–249; 623/17.11–17.16; 403/83, 92, 93, 100, 101
See application file for complete search history.

(56) References Cited

U.S. PATENT DOCUMENTS

| | | | |
|---|---|---|---|
| 6,770,096 B2 | 8/2004 | Bolger et al. | |
| 7,189,234 B2 | 3/2007 | Zucherman et al. | |
| 7,585,313 B2 * | 9/2009 | Kwak et al. | 606/249 |
| 7,988,708 B2 * | 8/2011 | Yeh | 606/248 |
| 8,246,655 B2 * | 8/2012 | Jackson et al. | 606/248 |
| 2003/0164635 A1* | 9/2003 | Battey et al. | 297/299 |
| 2007/0161992 A1 | 7/2007 | Kwak et al. | |

(Continued)

FOREIGN PATENT DOCUMENTS

| | | |
|---|---|---|
| WO | 03024298 | 3/2003 |
| WO | 2006008444 | 8/2006 |
| WO | 2007075470 | 7/2007 |

OTHER PUBLICATIONS

German Office Action dated Aug. 29, 2008 issued in related German Patent Application No. 102007052799.5.

(Continued)

*Primary Examiner* — Jan Christopher Merene
(74) *Attorney, Agent, or Firm* — Grossman Tucker Perreault & Pfleger, PLLC

(57) ABSTRACT

The invention relates to an implant that can be located between adjacent spinous processes of two vertebral bodies of a vertebral column in order to separate adjacent vertebrae from each other, where the implant displays four projections and can be located in a stabilizing position in which two projections can be located on opposite sides of the vertebral column and where, on each side, one of the two projections can be located along the vertebral column, laterally to an upper and a lower vertebra. According to the invention, the implant comprises two at least essentially rigid implant parts, each of which displays two projections that can be located on opposite sides of the vertebral column, where the two parts of the implant are connected to each other in articulated fashion by a joint located in the middle area thereof, such that, referred to the direction of insertion of the implant into the space between vertebral processes, each of the two implant parts displays a front and a rear projection, between which the joint is located.

14 Claims, 16 Drawing Sheets

U.S. PATENT DOCUMENTS

Figure 2:
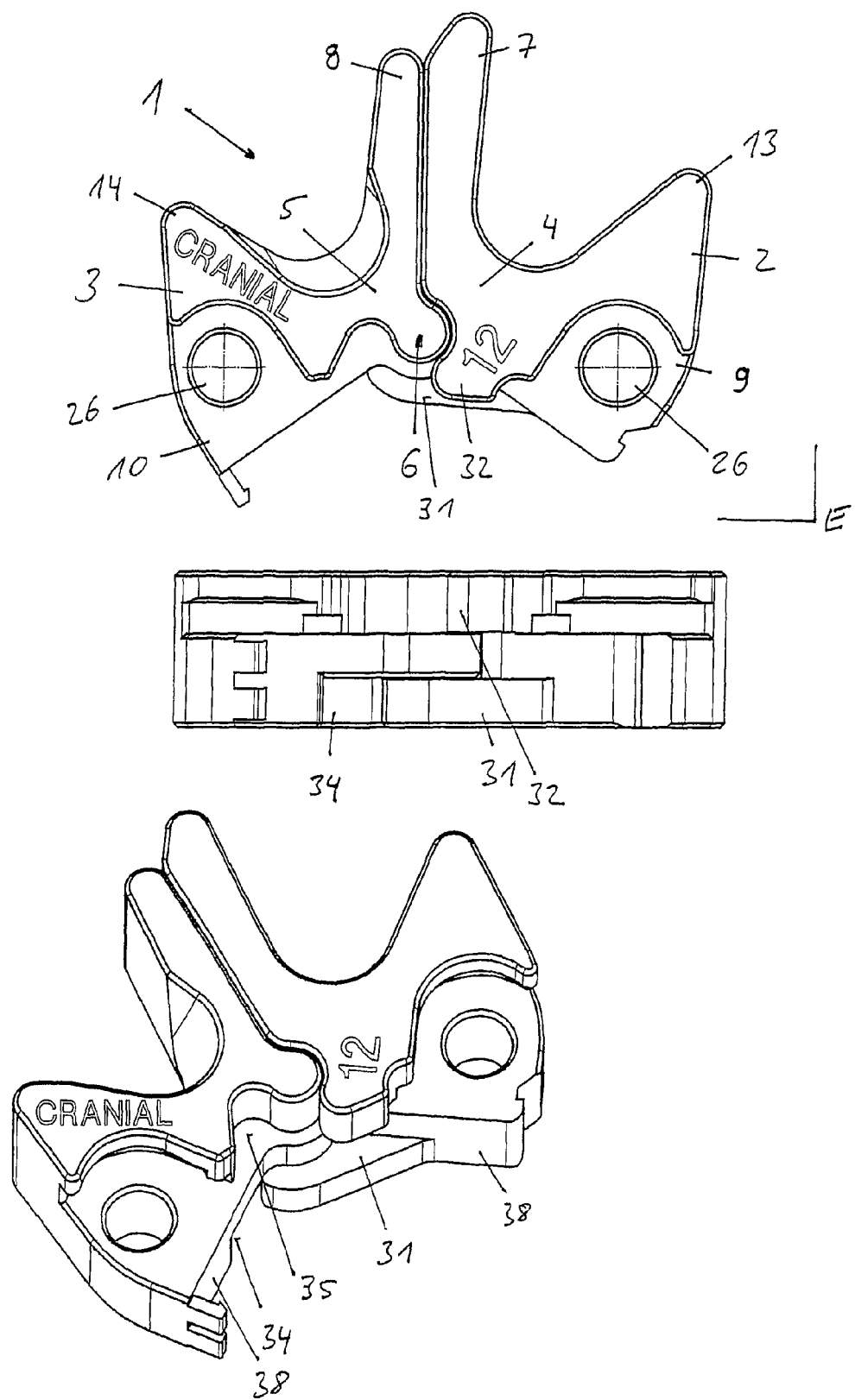

| | | | |
|---|---|---|---|
| 2007/0191959 A1* | 8/2007 | Hartmann et al. | 623/17.16 |
| 2007/0225724 A1 | 9/2007 | Edmond | |
| 2007/0233076 A1 | 10/2007 | Trieu | |
| 2008/0114455 A1* | 5/2008 | Lange et al. | 623/17.16 |
| 2008/0161818 A1 | 7/2008 | Kloss et al. | |
| 2008/0167657 A1* | 7/2008 | Greenhalgh | 606/90 |
| 2008/0208344 A1* | 8/2008 | Kilpela et al. | 623/17.16 |
| 2010/0179595 A1* | 7/2010 | Jackson et al. | 606/249 |
| 2011/0118788 A1* | 5/2011 | Hochschuler et al. | 606/278 |

OTHER PUBLICATIONS

International Search Report and Written Opinion dated Apr. 24, 2009 issued in related International Patent Application No. PCT/DE2008001755.

* cited by examiner

Fig. 1
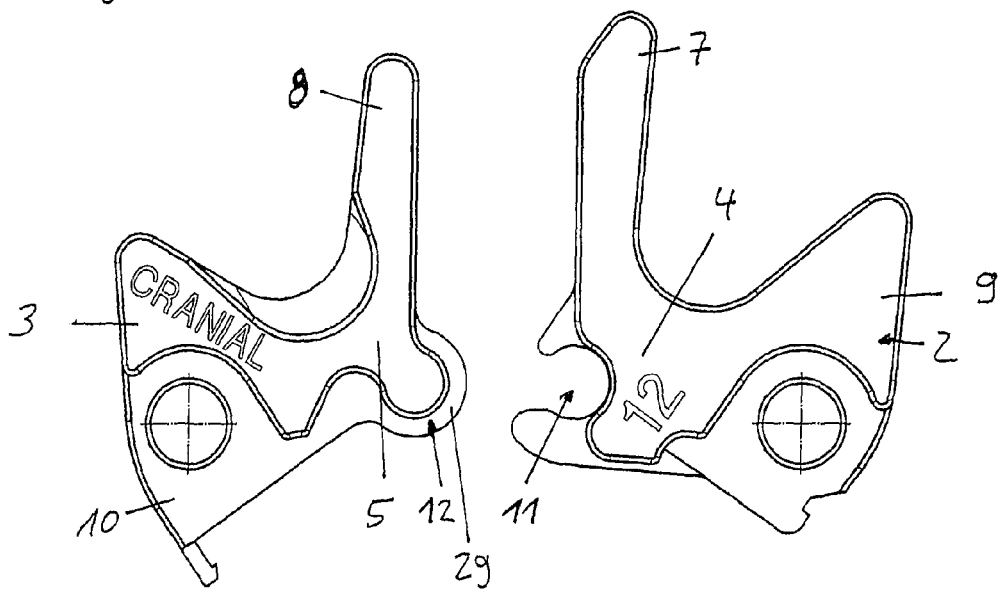
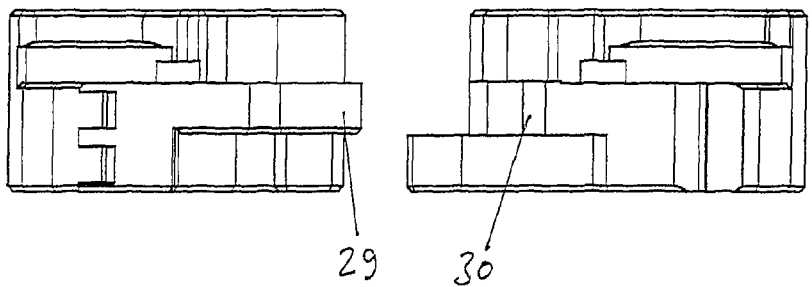
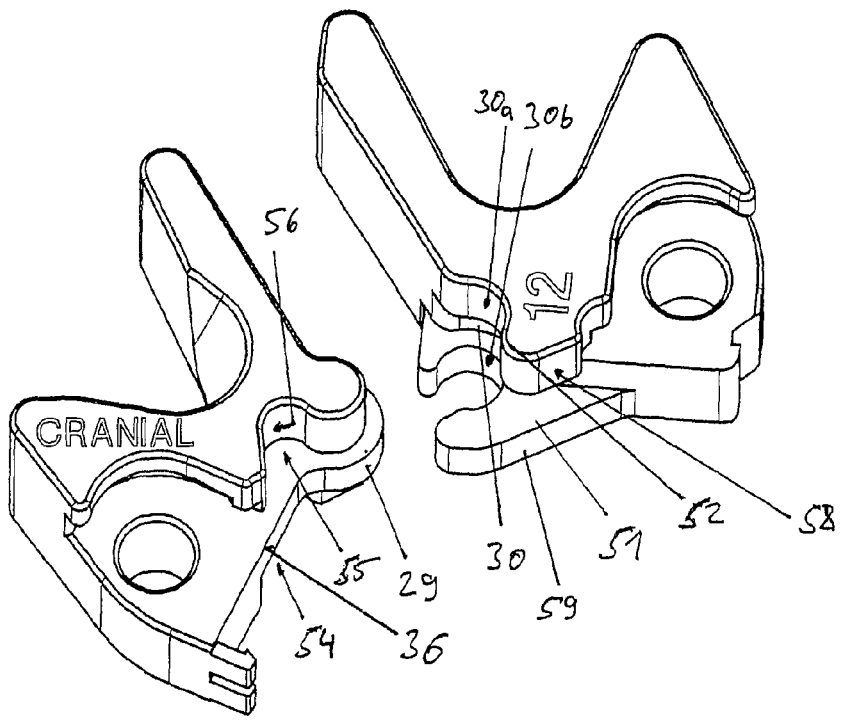

Fig. 3
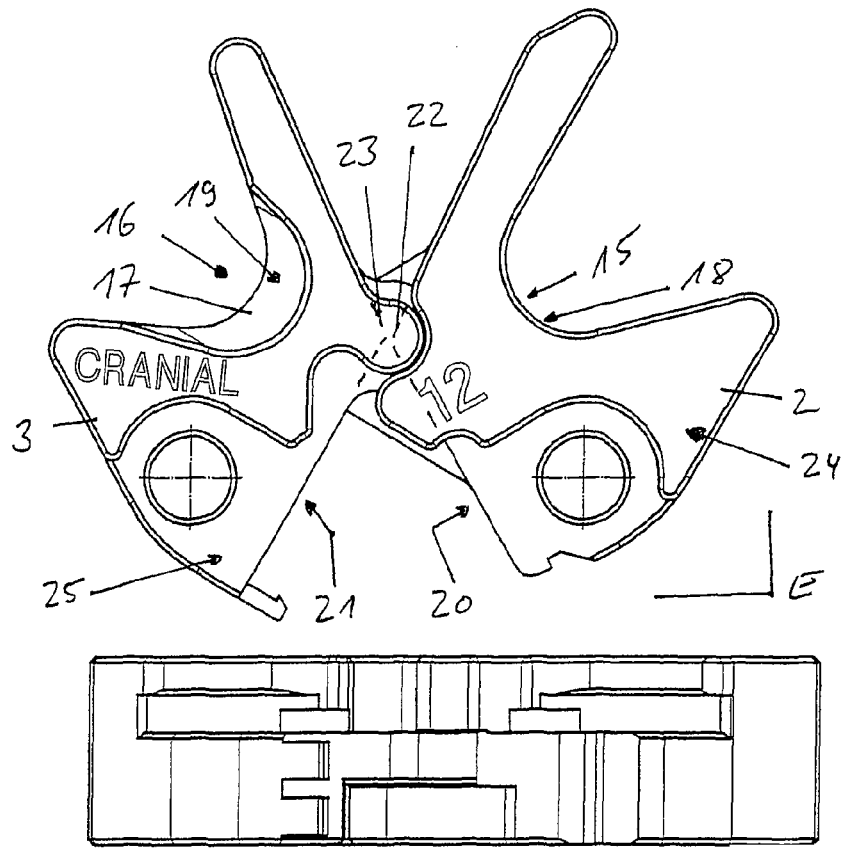
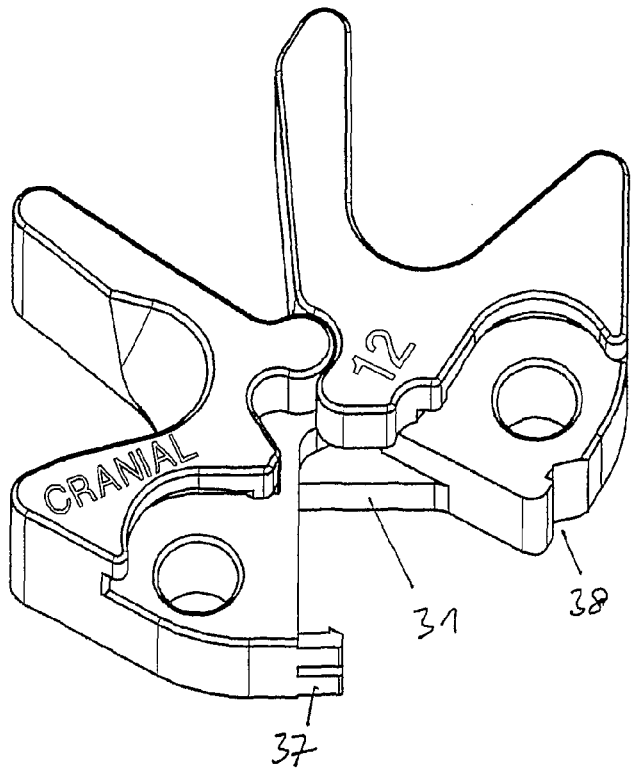

Fig. 4
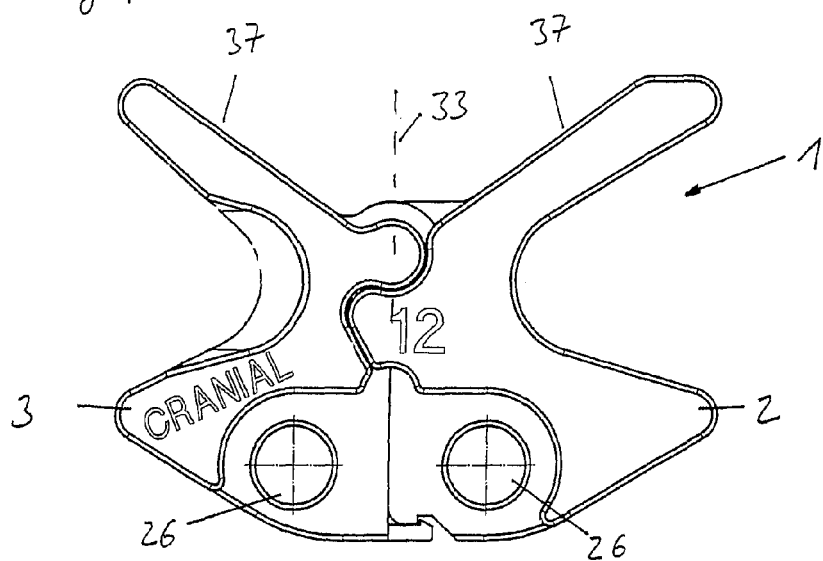
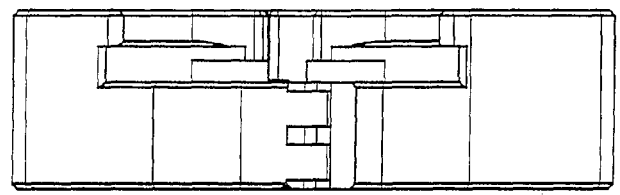
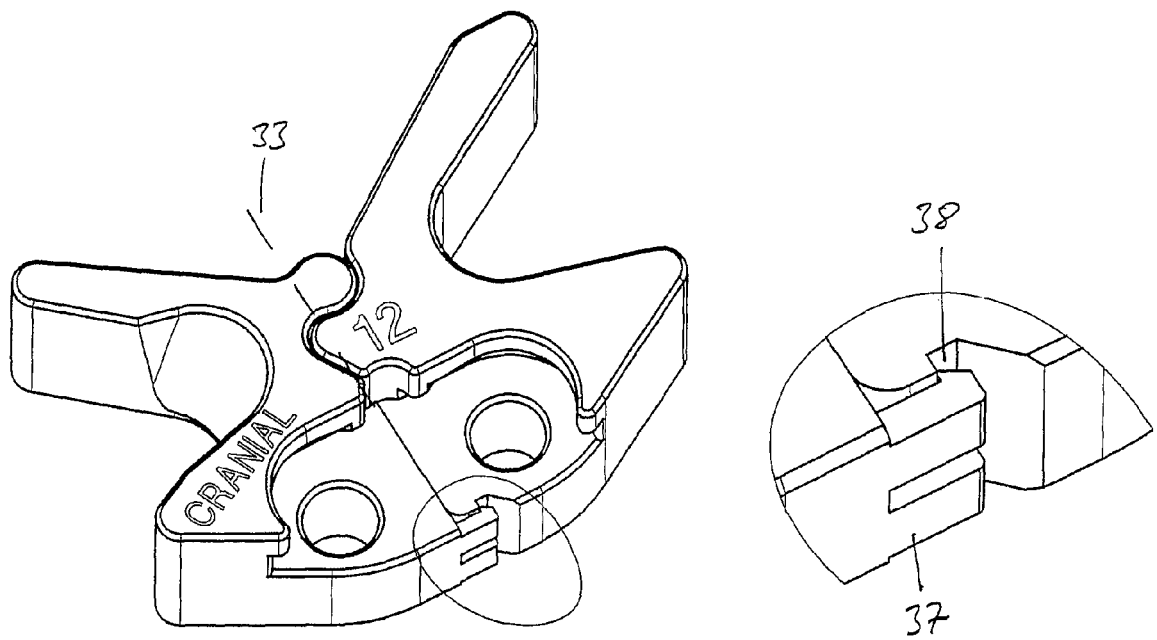

Fig. 5
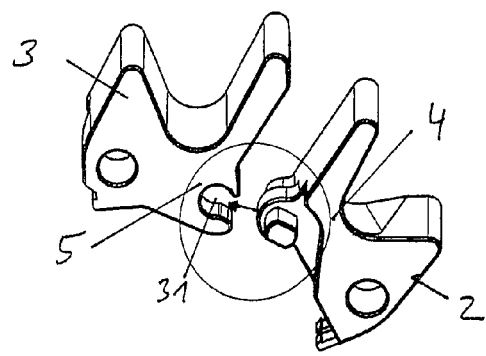
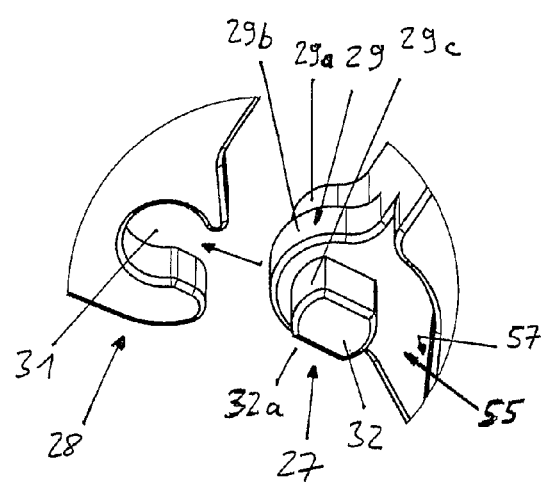
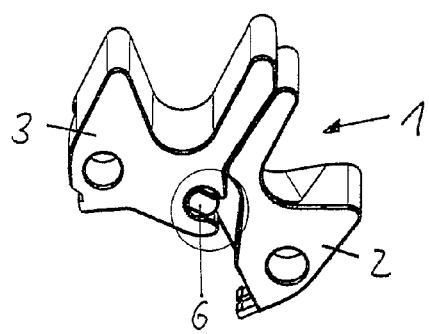
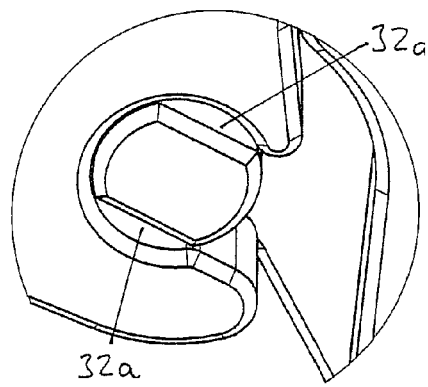
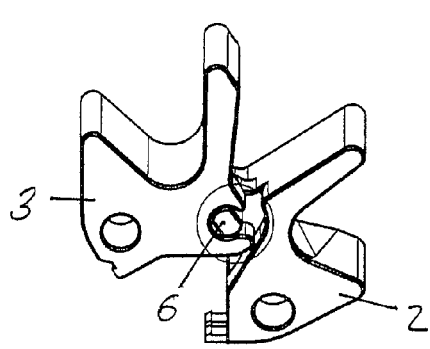
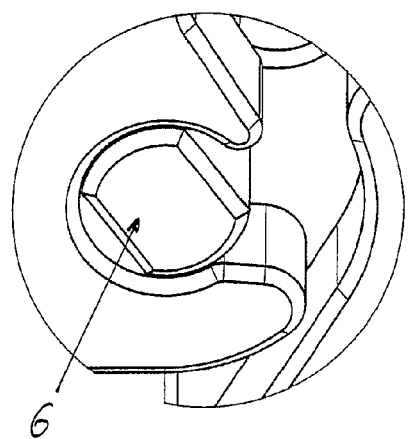

Fig.7
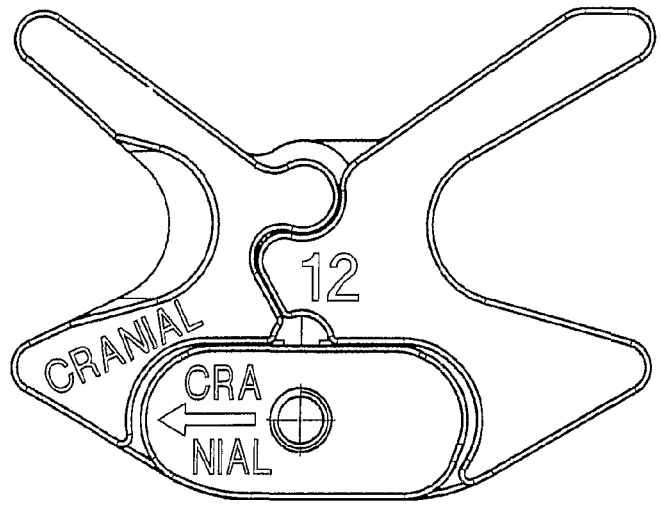
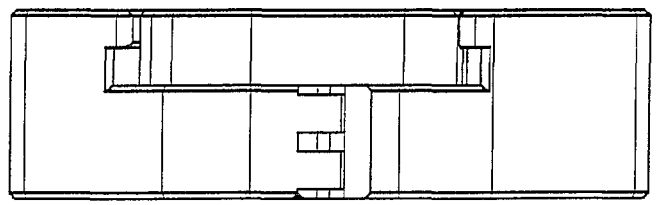
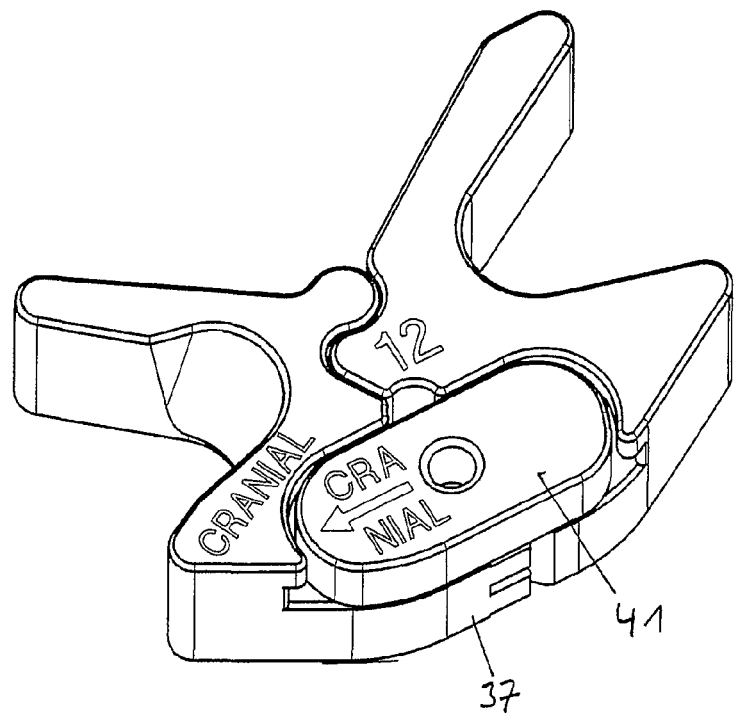

IMPLANT TO BE LOCATED BETWEEN ADJACENT SPINOUS PROCESSES

CROSS REFERENCE TO RELATED APPLICATIONS

The present application claims the benefit of the filing date of U.S. Provisional Application Ser. No. 60/990,080 filed Nov. 26, 2007 and German Application No. DE 10 2007 052 799.5 filed Nov. 2, 2007, the teachings of which are incorporated herein by reference.

The invention relates to an implant according to the generic part of claim 1. The invention furthermore relates to a tool for implanting an implant of this kind.

Implants of this kind are used to stabilize the vertebral column, in that respectively adjacent vertebrae are kept a minimum distance apart from each other by the implant and curvature of the vertebral column is prevented, or only permitted to a very limited degree, in the area of the inserted implants.

Diverse implants of this kind are already known. For example, WO 98/29047 describes an implant which displays a first unit with a body and a first wing displaying two projections that can be located on one side of the vertebral column, where a second wing is provided that can be located on the opposite side of the vertebral column and displays a central recess so that it can be slid onto the body such that the vertebral column is stabilized on both sides. However, the handling of these implant parts, which requires bilateral manipulation on the vertebral column, is awkward for the surgeon. Moreover, inserting the body into the recess of the second wing requires very high precision when fitting the implant.

US 2005/0203512 A1 describes a one-piece implant where the main body, which can be located between vertebral processes, displays four deformable projections that are made of a memory metal, such that, following insertion into the space between the vertebral processes, they automatically return to their original position in order to be located laterally adjacent to the vertebrae. However, the use of memory metals of this kind is very expensive and, in addition, such metals can only absorb limited forces, meaning that sufficient stabilization of the vertebral column is not ensured under all circumstances.

US 2004/0220568 A1 describes diverse embodiments of implants, including an implant with a dimensionally stable configuration, which displays a central body with four processes that is made of a rigid material. However, the rigid design of this implant makes it awkward to implant between vertebral processes, and it is virtually impossible to adapt the implant to the individual anatomy of the respective patient. Other versions describe implants with deformable projections, or implants with strut-like projections extending upwards and downwards in relation to the vertebral column, whose retaining forces are, however, limited, or whose handling is awkward.

The object of the invention is to create an implant that no longer displays the disadvantages of the implants known hitherto, is easy to handle, can particularly be inserted into the space between the vertebral processes of adjacent vertebrae, can reliably absorb even high forces, and that is easy to manufacture and consists of few component parts.

This object is solved by an implant according to claim 1. The implant comprises two at least essentially rigid implant parts, each of which displays two projections that can be located on opposite sides of the vertebral column, where the two parts of the implant are connected to each other in articulated fashion by a joint located in the middle area thereof. Each of the two rigid implant parts thus provides a front and a rear projection that can be located on opposite sides of the vertebral column. In a pivoted position of the two parts of the implant, corresponding to an insertion position of the implant, the two front projections to be inserted into the space between vertebral processes can then be brought into contact with each other, or at least positioned closely adjacent to each other, such that they can be inserted into the space between the vertebral processes transversely or essentially perpendicularly to the vertebral column. Once the front projections have at least essentially passed the two vertebral processes located on adjacent vertebrae, and further progress is prevented by the vertebral column, the two implant parts connected to each other in articulated fashion can be pivoted relative to each other, such that, by preferably simultaneous movement of the four projections relative to each other, the implant can be moved into its stabilizing position, in which the two front projections and the two rear projections are respectively spaced apart from each other and located on both sides of the vertebral column, laterally adjacent to the upper and lower vertebra. The two rigid implant parts are capable of absorbing high vertebral forces. Furthermore, the implant is easily inserted into a space between vertebral processes, particularly into the space between adjacent spinous processes of two vertebral bodies of a vertebral column, and moved into its stabilizing position. Moreover, the implant can consist of just a few component parts. Implants according to the invention can particularly be used to stabilize and relieve the lumbar column. The two parts of the implant can each be of once-piece design.

Further advantageous embodiments are indicated in the subclaims.

For the purpose of the invention, the "front projections" of the implant parts are always those located at the front in the direction of implant insertion into the intervertebral space, the "rear projections" of the implant parts always being those located at the rear in the direction of implant insertion into the intervertebral space.

The two parts of the implant can be connected to each other in articulated fashion, such that the two front projections of the two implant parts can be at least essentially brought into contact with each other and inserted into the space between the vertebral processes in this position, where, by applying force to the two rear projections relative to each other, said projections perform a movement, as a result of which, due to coupled motion, the front projections can be spread apart in order to be positioned at least roughly laterally on the two adjacent vertebral bodies. At the same time as this, the two rear projections can also be positioned against the two adjacent vertebral bodies, such that the implant is located in its stabilizing position. Owing to the direct coupling of the front and rear projections and the forced spreading of the front projections when pressure is applied to the rear projections in their pivoting direction towards the stabilizing position, further force-transmitting means can be dispensed with and the structural design of the implant can be particularly simple. Moreover, the two rigid implant parts permit absorption of high forces and precise positioning of the implant parts in their stabilizing position. In addition, both insertion of the implant into the space between the vertebral processes and also the spreading of the front projections, as seen in the direction of insertion, can be performed from the same side of the vertebral column, meaning that handling is facilitated.

The implant parts are preferably connected directly to each other in articulated fashion.

According to one embodiment, the two implant parts can each be of at least essentially V-shaped design, each displaying a middle vertex area, where the two vertex areas of the implant parts are arranged facing each other. The two legs of the V-shaped implant parts extend in each case from the vertex areas or vertices. The joint connecting the two implant parts to each other can be located in the region of the vertex areas or in the region of the two vertices of the implant parts. The joint can generally be located in the middle area of the two implant parts. The essentially V-shaped design can also include an essentially U-shaped modification, where the implant parts can display an arched transitional area on the sides located opposite each other and/or facing towards the vertebral bodies. The two legs of the at least essentially V or U-shaped implant parts can converge in the vertex area or at the vertex of the parts, and they can also be separated from each other by a middle area, where appropriate. The joint areas on one or both implant parts can be integrated in the implant parts in such a way that the joint areas only partly project laterally from the peripheral contour of the respective part in the direction of the other part and are at least partly accommodated within the peripheral contour of the part. The joint areas can thus be designed as laterally engaging areas of the two implant parts.

The side of the two implant parts facing towards the vertebral processes and/or the side facing away from them can in each case be of essentially V-shaped design, such that the two projections of the respective implant part can be located on both sides of the vertebral column and include an angle relative to the longitudinal direction of the vertebral column. The V-shaped design can include an essentially U-shaped or other modification. The two lateral surfaces of the V-shaped implant part, which face the adjacent vertebral process or the respectively other implant part, can include different angles. This can in each case apply to one or both of the implant parts. On one of the legs, preferably the leg that is in front in the direction of insertion, the two lateral surfaces can be located virtually parallel to each other, or include only a small angle, e.g. of $\leq 20\text{-}30°$ or $\leq 5\text{-}10°$. On the other projection, preferably the "rear" projection in the direction of insertion, the two lateral surfaces of the implant part can include an angle with each other, such that the implant part can display a plateau-like wider area at this point. The side of the implant opposite the vertebral processes can include an angle of approx. 45-90°, preferably approx. 45-75°, particularly approx. 60°. The side of the respective implant part facing towards the respectively adjacent implant part can include an angle of 100-150°, preferably 110-150°, e.g. approx. 125°. The plateau-like wider area located on the one end of the implant part, which can be of essentially angular or arched design, can extend over an angular range of $\leq 120°$, e.g. approx. 30-90°, preferably 45-80°, particularly approx. 60-70°, or also $\leq 30°$.

As a result of this, the implant can, on the whole, easily be inserted into the space between vertebral processes and moved into a stabilizing position in which, on the one hand, the rear legs of the two implant parts, as seen in the direction of insertion, are in contact with each other, preferably forming a flat contact surface, and, on the other hand, the outer sides of the implant parts, facing the vertebral processes, surround the vertebral process closely enough to achieve the desired stabilization of the vertebral column. Furthermore, the sides of the implant parts diagonally opposite each other can include an angle of approx. 140-220°, preferably approx. 155-205° or approx. 180°. The outer sides of the two implant parts connected to each other through the joint area can thus be of at least approximately straight design. Thus, the side of the rear projection facing away from the vertebral process can, when in the insertion position, be designed essentially as an extension of the side of the rear projection of the other implant part facing towards the vertebral process. In the implantation position, the same applies to the side of the rear projection facing towards the vertebral process and the side of the front projection facing away from the vertebral process.

Preferably, by pivoting the two implant parts relative to each other, one of the two lateral surfaces of the respective implant part, located on both sides of the joint, can in each case be brought into contact with the respectively other implant part in a contact area, preferably by means of a contact surface that can extend over at least essentially the full height and/or length of the projections.

Thus, to fit the implant, the two front projections are first moved into a pivoting position (insertion position) in which they are adjacent to each other apart from a small gap, or in lateral contact with each other, such that they can be inserted into the space between vertebral processes. The two rear projections are spread apart in this context, such that the implant is expanded in V-shaped fashion and has, for example, an approximately T-shaped form. After insertion of the front projections, where appropriate until the implant is stopped by the vertebral processes, the rear projections are pivoted towards each other, reducing the spreading angle, up to a small distance apart, where appropriate, or until the two rear projections come into contact with each other. As a result, the front projections are spread apart to an equal extent and can be moved into a position laterally adjacent to the vertebral processes of the upper and lower vertebra until the implant reaches its stabilizing position. A given vertebral process of a vertebra is thus laterally stabilized by the front and rear projection of the same implant part.

Where appropriate, the implant can be of scissor-like design, where the joint is located in the middle area of the two implant parts and connects them to each other in cross-over fashion. The implant is thus designed in such a way that, if the front projections are a small distance apart from each other or in contact with each other, this also applies to the two rear projections. In its insertion position, the implant can then be inserted into the space between vertebral processes transversely or perpendicularly to the vertebral column. To move the implant into its stabilizing position, the two rear projections can be moved apart from each other and spread open by pivoting the two implant parts relative to each other, such that the front projections are also moved apart from each other at the same time and the implant is thus spread open on both sides of the vertebral column. To open and close the two implant parts, it suffices merely to apply pressure to the rear projections in order to pivot them towards or away from each other. Here, too, the rear projections can display plateau-like wider areas, such that, in the stabilizing position of the implant, the front and rear projections, located on both sides of the vertebral processes, in each case include an angle $\leq$approx. 90° with each other, e.g. approx. 45-60° or smaller.

However, it goes without saying that, where appropriate, the two front projections can also be actuated after insertion of the implant into the space between the vertebral processes, in order to move the two rear projections into their stabilizing position with them by means of coupled motion.

In general, the two front projections, as seen in the direction of insertion, can spread open to an angle of 60-150°, preferably 70-150° or approx. 80-130°, particularly preferably to an angle of 100-130° or approx. 110-120°, when the implant is in its stabilizing position.

The pivoting angle of the two implant parts relative to each other can be in the range of 60-150°, preferably in the range of 90-130° or approx. 110-120°, without limitation. This can in each case be the maximum possible pivoting angle or the pivoting angle for moving the implant parts from their insertion position into their stabilizing position.

The two essentially rigid implant parts can display a stiffness such that they are at least essentially dimensionally stable during implantation and, when stabilizing a vertebral column, particularly also when subjected to the movement of the respective patient. The implant parts can, for example, be made of a suitable metal or alloy, such as titanium, or also of a dimensionally stable plastic material or a suitable composite.

Advantageously, the implant parts engage each other in the manner of a comb in order to couple to each other in a manner preventing displacement transverse to their pivoting plane.

On the rear projections as seen in the insertion direction, the two implant parts may display plateau-like wider areas that can display interacting functional elements.

The invention furthermore relates to a tool for implanting an implant according to the invention.

According to the invention, the tool for implanting an implant may display two catches that are displaceable relative to each other and adapted to each couple, in a coupling position, to one of the two rear projections, as seen in the direction of insertion of the implant, of the implant in its insertion position, where the catches are laterally spaced apart from each other in this position and located adjacent to each other in an implantation position, such that the coupling implant is in its stabilizing position, wherein a positive guide is provided for the catches, by means of which the displaceable catches can be moved from their coupling position to their implantation position, and wherein an actuating means is provided for moving the catches along the positive guide.

Alternatively or simultaneously, according to the invention the tool for implanting an implant may be designed in that two catches are provided that can be coupled to the two rear projections of the implant in their coupling position, wherein a positive guide is provided, in which the catches are guided, wherein actuating means for moving the catches along the positive guide are provided, by means of which the catches can be moved from their insertion position, in which they display a first gap d1 and in which the implant can be inserted into the space between vertebral processes, into their stabilizing position, in which they display a second gap d2 and the implant stabilizes the vertebral column, and wherein the actuating means display a device transmitting tensile and pressure forces, as well as a dimensionally stable actuator device that couples by means of actuator elements on the catches, and that can be moved relative to the catches by the actuating means.

The tool displays two catches, the distance between which is variable, where these catches can be designed as catch pins that can end at least roughly at the same height. In a coupling position, the catches can act on the two rear projections of the implant when it is in its insertion position, and the catches can be moved into an implantation position, in which the implant is in its stabilizing position. Depending on the design of the implant, the catches can be a greater or smaller distance apart from each other in the coupling position than in the implantation position. In this context, the catches are located in a positive guide in order to be able to displace them from their coupling position to their implantation position. In addition, an actuating means is provided for forcibly moving the catches together along the positive guide. For displacing the catches, the tool can display an at least essentially rigid actuator plate with actuator elements acting on the catches, e.g. on their retaining areas in the positive guides. The actuator elements can be designed such that, in the event of movement of the actuator plate in its principal plane, particularly displacement towards the implant or away from the implant, they bring about a change in the distance between the catches in order to move them from the coupling position into their implantation position. In this context, the actuator elements can be designed as guides for the catches or their retaining areas that include an angle relative to the positive guides of the catches. As a result of this, the implant according to the invention can easily be moved from its insertion position into its stabilizing position.

According to the invention, the actuating means may comprise an actuator device in the form of an actuator plate with a principal plane, which is movable relative to the positive guide and displays actuator elements acting on both catches that are designed in such a way that, as a result of movement of the actuator plate in its principal plane, they bring about a change in the distance between the catches.

According to the invention, the actuator plate may display two guides that are located in a plane, arranged to include an angle with each other and, starting from a base where the distance between the guides is such that the catches located at the base are in their coupling position, converge in a vertex, where the catches at least roughly located at the vertex are in their implantation position.

According to the invention, the guides may have a linear profile and the vertex is located in the middle area of the actuator plate.

According to the invention, the actuator plate can be displaced relative to the positive guides in translatory fashion in a plane.

According to the invention, the positive guides of the catches may intersect the guides of the actuator plate on both sides of the vertex.

According to the invention, the positive guides may be linear guides that run at an angle to the guides of the actuator plate.

According to the invention, the positive guides may be located in a plane holding structure located plane-parallel to the actuator plate.

According to the invention, the tool may be designed in such a way that, in the actuating position of the tool on the implant, the actuating means is oriented transversely to the vertebral column of the patient to be treated and/or transversely to the principal plane of the patient, and is moved transversely to the vertebral column and/or transversely to the principal plane of the patient when the tool is actuated.

The actuating means can display a handle for one-hand actuation of the tool, where the actuating means are designed in such a way that, when the tool is actuated, the handle is located in an immovable position relative to the positive guide of the catches and/or relative to the vertebral column of the patient on which the implant is fitted. The tool can be designed in such a way that, in the actuating position of the tool on the implant, the actuating means is oriented transversely to the vertebral column of the patient to be treated and/or transversely to the principal plane of the patient, and is moved transversely to the vertebral column of the patient to be treated and/or transversely to the principal plane of the patient in order to open or close the implant by means of the tool.

Figure 6:
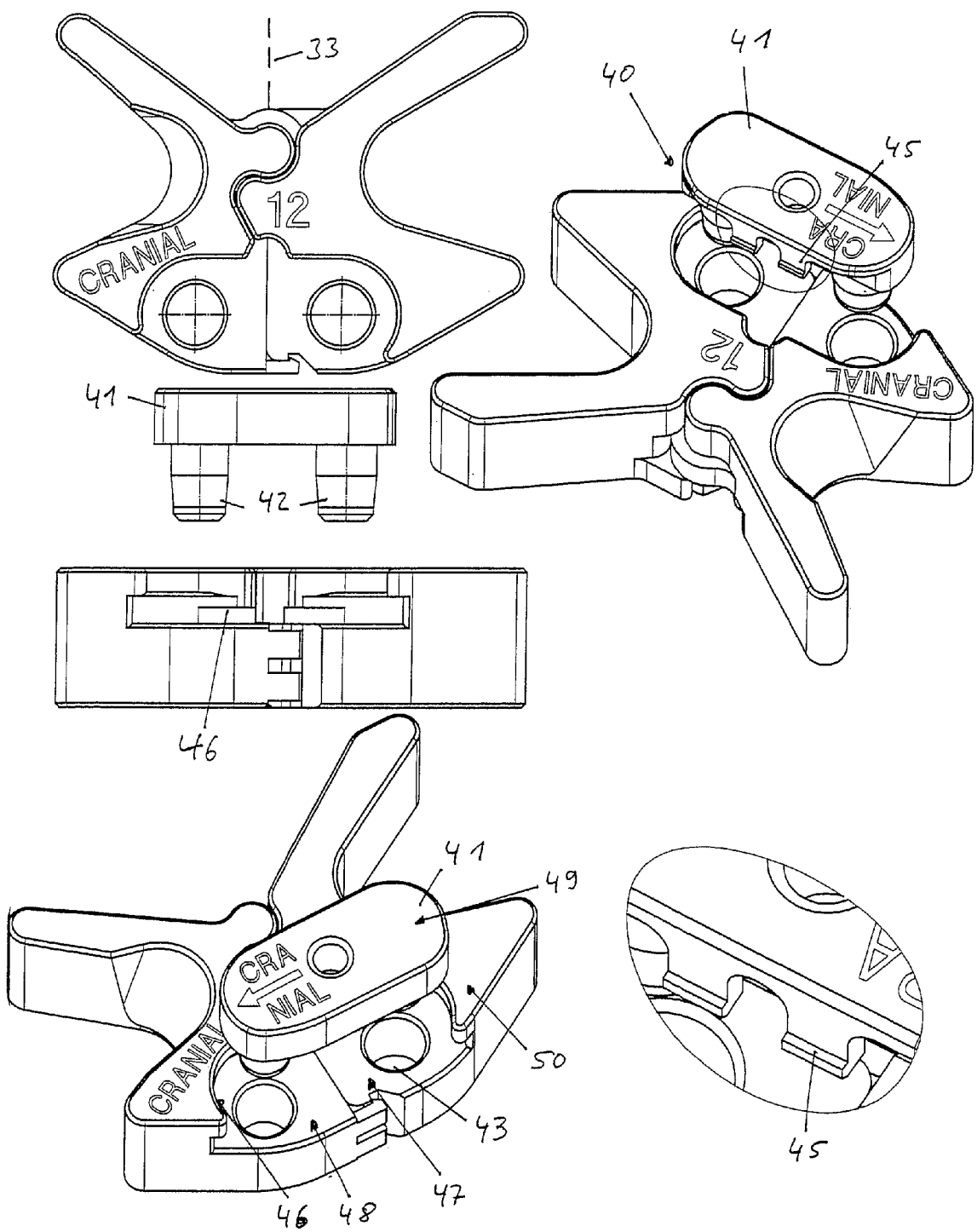
Figure 9:
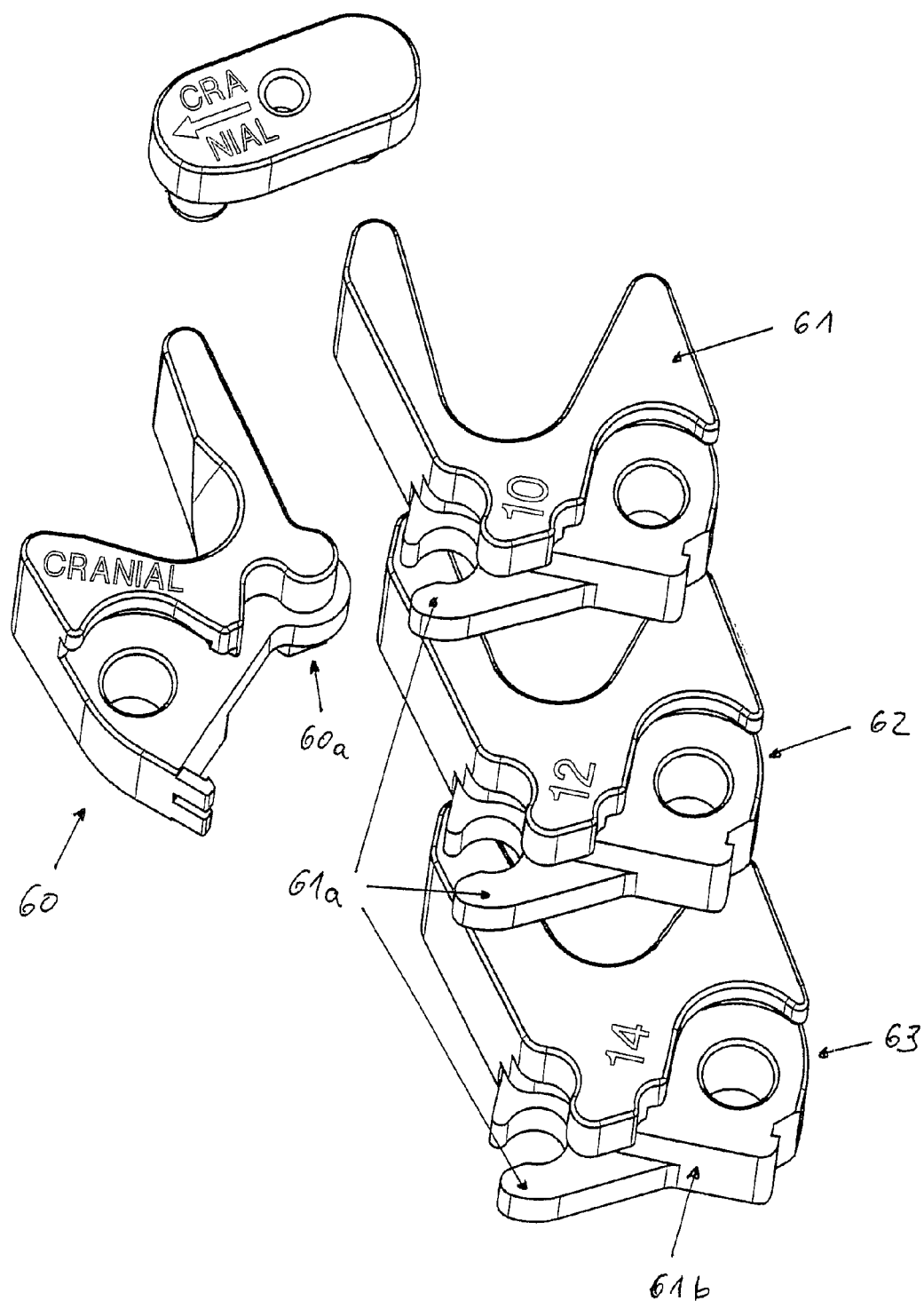
Figure 10:
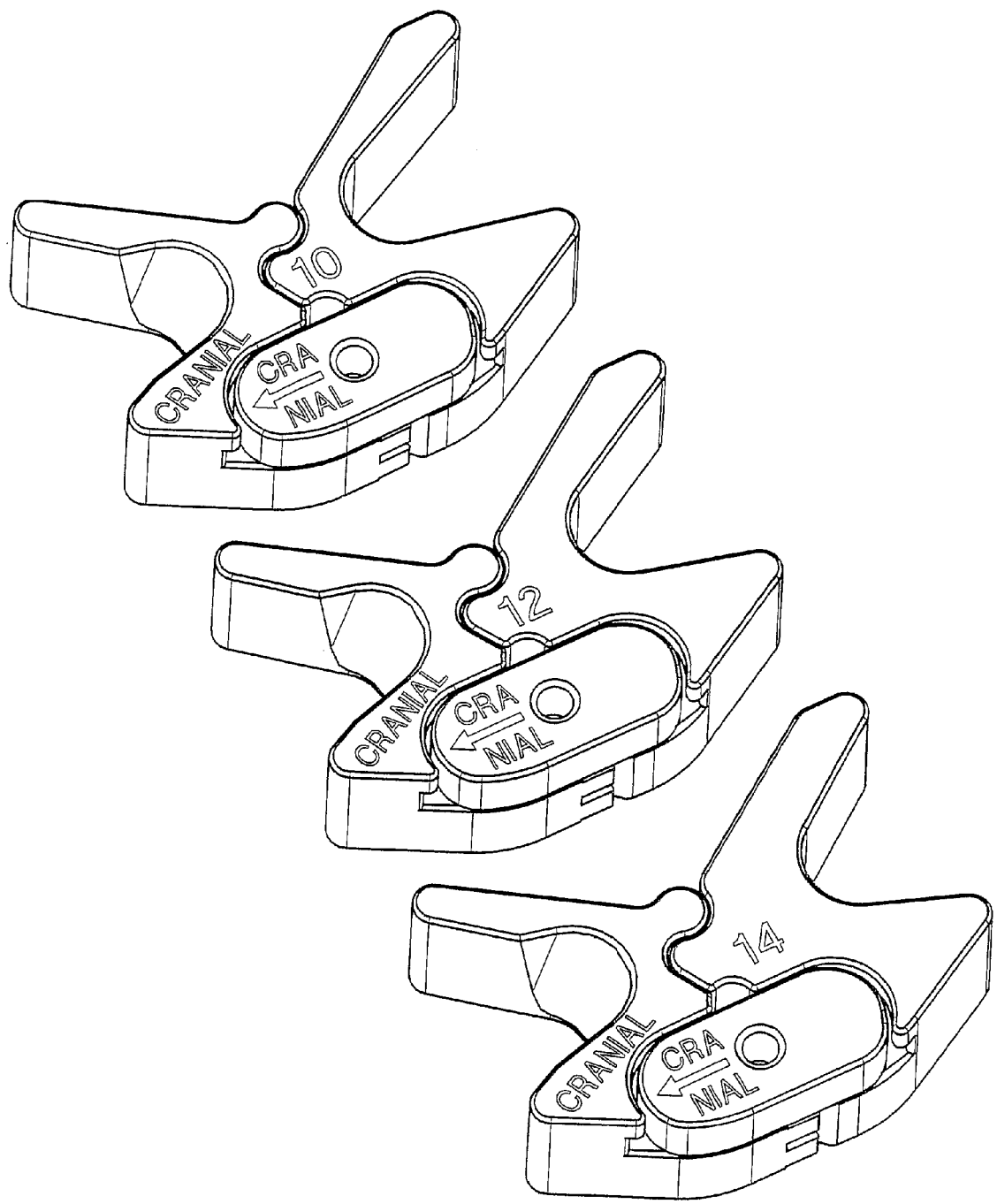
Figure 11:
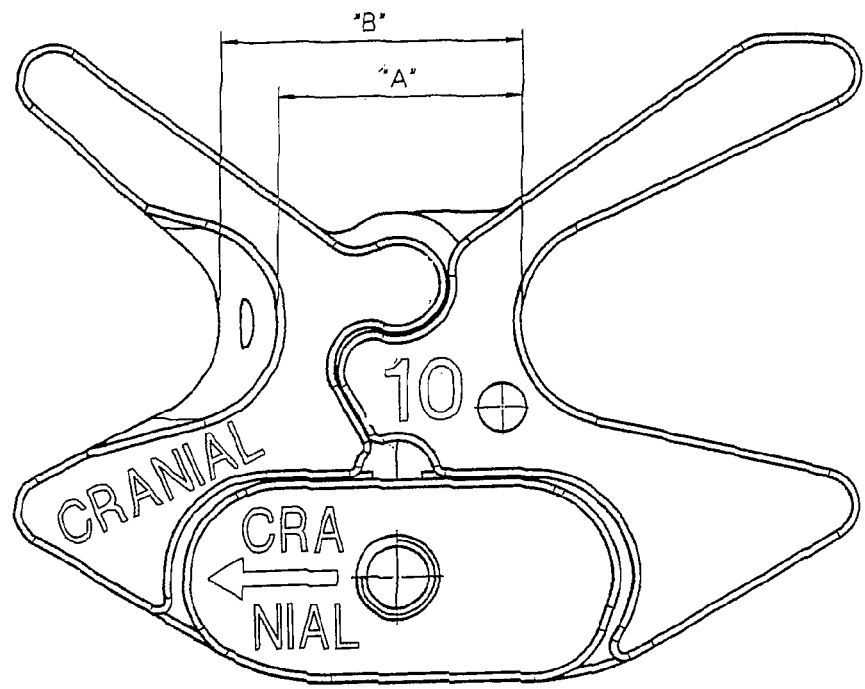

The invention is described in more detail below and an example explained based on the Figures, although the explanations below are not to be interpreted as restricting the extent of protection of the invention. The Figures show the following:

FIG. 1: A representation of an implant according to the invention with two implant parts in dismantled state, in a top view (FIG. 1a), a side view (FIG. 1b), and a perspective view (FIG. 1c), FIG. 2: An implant according to FIG. 1 in assembled state in insertion position, in a top view (FIG. 2a), a side view (FIG. 2b), and a perspective view (FIG. 2c), FIG. 3: An assembled implant according to FIG. 1 in partly closed state, in a top view (FIG. 3a), a side view (FIG. 3b), and a perspective view (FIG. 3c), FIG. 4: An assembled implant according to FIG. 1 in stabilizing position, in a top view (FIG. 4a), a side view (FIG. 4b), and a perspective view (FIG. 4c), as well as in a detail view (FIG. 4d), FIG. 5: As implant according to FIG. 1, in dismantled state with a detail view (FIGS. 5a, 5b), in assembled state with a detail view (FIGS. 5c, 5d) and in partly closed pivoting position with a detail view (FIGS. 5e, 5f), FIG. 6: A representation of the implant according to FIG. 1 in stabilizing position, with lock to be fitted, in various views, FIG. 7: An implant according to FIG. 6 with mounted lock, in a top view (FIG. 7a), a side view (FIG. 7b) and a perspective view (FIG. 7c), FIG. 8: An implant according to FIGS. 1 to 7 in implanted state on the vertebral column, Fig. 9: A set (system) of implant parts for constructing various implants, in dismantled state, Fig. 10: Various implants, constructed from the set (system) according to FIG. 9, in completely assembled state, FIG. 11: A top view of an implant according to FIG. 1, FIG. 12: A schematic representation of an alternative embodiment of an implant, in insertion position (FIG. 12a) and in stabilizing position (FIG. 12b), FIG. 13: A schematic representation of a further alternative embodiment of an implant, in insertion position, FIG. 14: A representation of an implantation tool with implant, in insertion position (FIG. 14a), in a side view (FIG. 14b), and a front view (FIG. 14c), FIG. 15: An implantation tool with implant according to FIG. 14, in stabilizing position (FIG. 15a), in a side view (FIG. 15b), and a front view (FIG. 15c), FIG. 16: A representation of the tool according to FIG. 14, in an exploded view.

Figure 8:
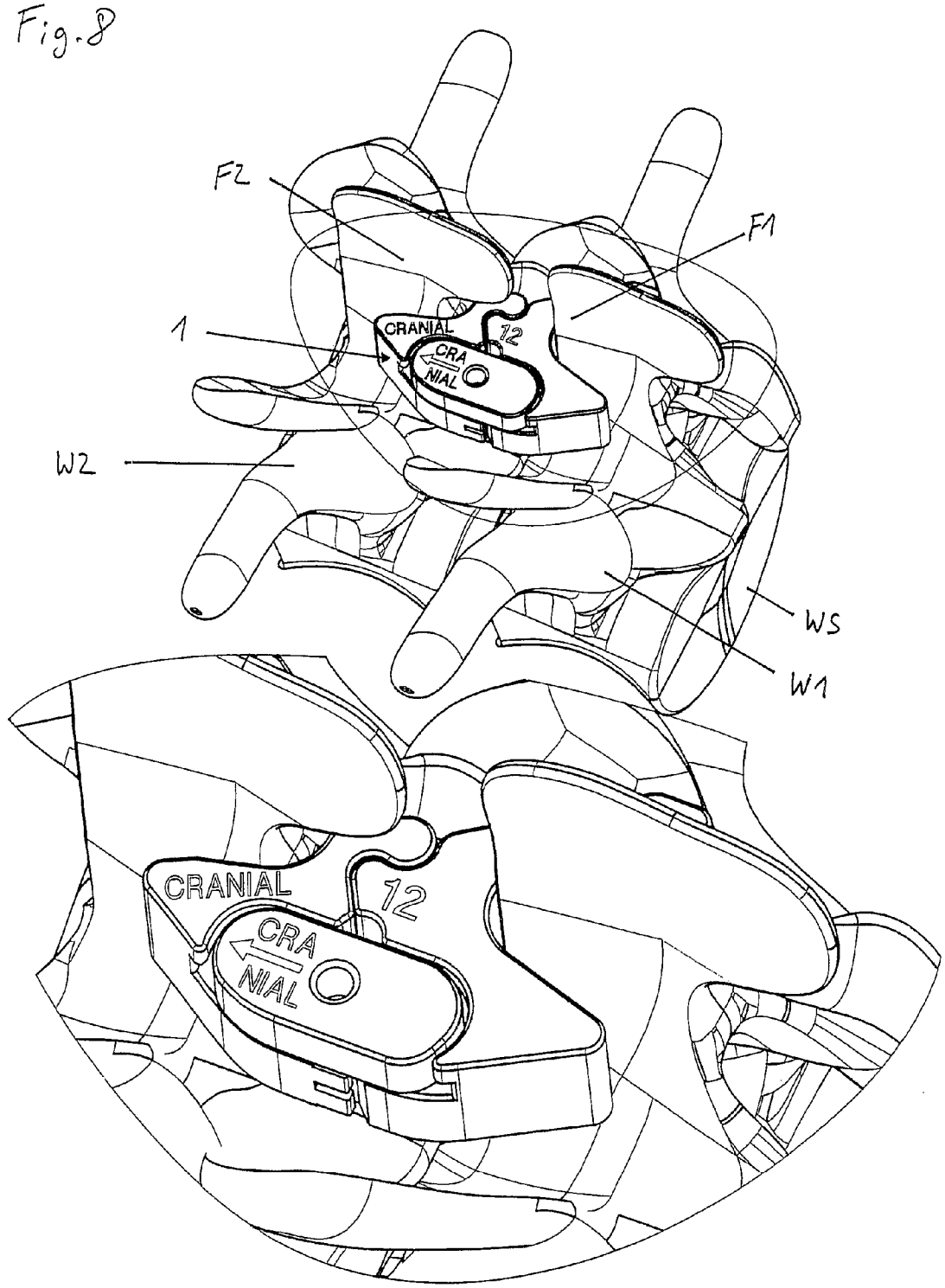

FIGS. 1 to 8 show an implant 1 that can, as illustrated in FIG. 8, be positioned between adjacent vertebral processes F1, F2 (more precisely: in the space between adjacent spinous processes of two vertebral bodies of a vertebral column) in order to separate adjacent vertebrae from each other or stabilize their position. In this context, implant 1 displays at least two essentially rigid implant parts 2, 3, which are connected by a joint 6, located in their middle area 4, 5. The implant parts thus constitute separate parts, although it is also possible, in the framework of the invention in general, for them to be permanently or inseparably connected to each other, e.g. by means of a suitable design of the joint, such as with a hinge pin. In this context, the implant displays four projections 7, 8, 9, 10, where each implant part encompasses a front and a rear projection, such that pairs of projections 7, 8 and 9, 10 can be located on opposite sides of vertebral column WS. On either side of the vertebral column, one of the projections can be located laterally to an upper vertebra W1 (in the direction of extension of the vertebral column), and another projection, located on the adjacent implant part, laterally to a lower vertebra W2 in the direction of the vertebral column.

When the two implant parts 2, 3 connected in articulated fashion are arranged as shown in FIG. 2, implant 1 is in its insertion position, such that it can be inserted laterally into the space between vertebral processes F1, F2, with front projections 7, 8, as seen in the direction of insertion, positioned transversely or perpendicularly to the vertebral column. In this context, the two front projections 7, 8 of the two implant parts are in contact with each other, at least essentially or, as illustrated, over their full surface. The two implant parts are connected to each other in articulated (more precisely: pivoting) fashion by the two joint areas 11, 12 (FIG. 1) on the middle areas of the implant parts. After insertion of front projections 7, 8, preferably until the middle areas of the implant parts, or the forwardly projecting end areas 13, 14 of the rear projections, at least approximately run up against the vertebrae, implant parts 2, 3 are, as shown in FIG. 3, pivoted relative to each other towards their stabilizing position, such that, seen in the direction of insertion, the implant simultaneously opens at the front and closes at the rear. By coupled motion, the front and rear projections 7, 8 and 9, 10 of the rigid implant parts are thus moved into their stabilizing position (see FIG. 4), in which the front and rear projections of the two implant parts 2, 3 are spaced apart from each other and located on both sides of vertebral column WS, laterally adjacent to, or laterally in contact with, the respectively upper and lower vertebra W1, W2. In stabilizing position, the implant thus has an essentially cross-shaped form. With the given embodiment, the implant has an essentially T-shaped form when in its insertion position according to FIG. 2, such that the middle leg can be inserted into the space between vertebral processes.

According to the practical example (see FIG. 3), sides 15, 16 of the implant parts facing towards the vertebral processes each include an angle of approx. 60° in order to provide areas for receiving the vertebral processes. The base of the elliptical free spaces is curved in this instance. The cranial base 17 can display an indentation 19, widening towards the upper side of the implant facing away from the vertebral column, for receiving the vertebral or spinous process. Base 18 of the opposite free space can be designed perpendicularly to pivoting plane E. The bases 17, 18 of the free spaces receiving the vertebral processes on both sides can thus generally be of different designs. The side 20, 21 of the respective implant part facing towards the respectively adjacent implant part can display an angle of approx. 125°, where the vertices of the angles 22, 23 (broken line) are arranged facing or adjacent to each other. The preferably plateau-like wider area 24, 25 located on the one end of the implant part, which can be of essentially angular or arched design, can extend over an angular range of approx. 60-70°. The upper and lower sides of the wider areas can be of essentially plane design, although this is not obligatory. In the stabilizing position of the implant, the two front projections can open to an angle of approx. 110-120°.

Figure 13:
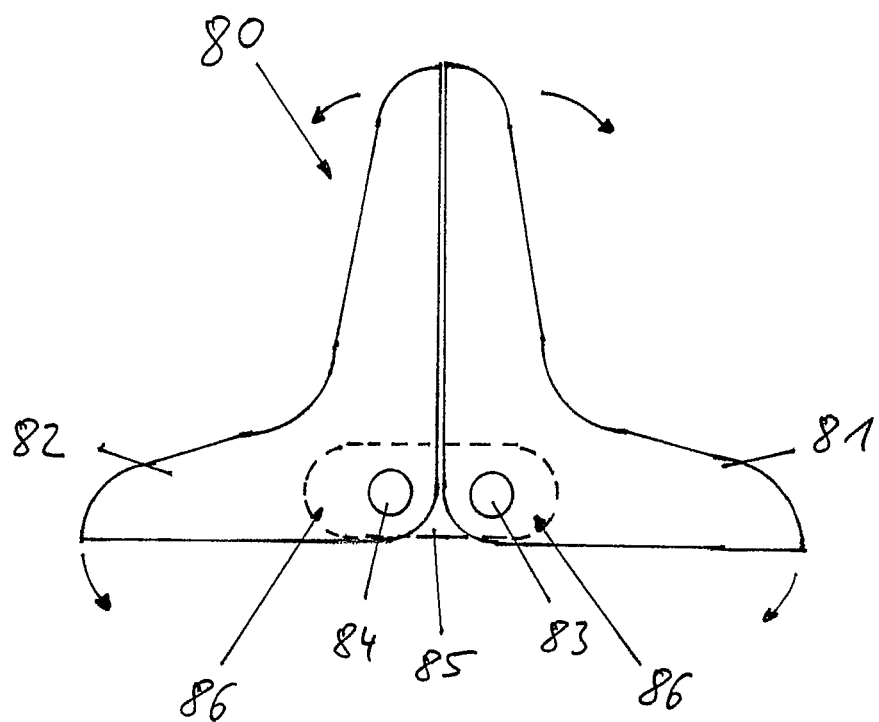
Figure 14:
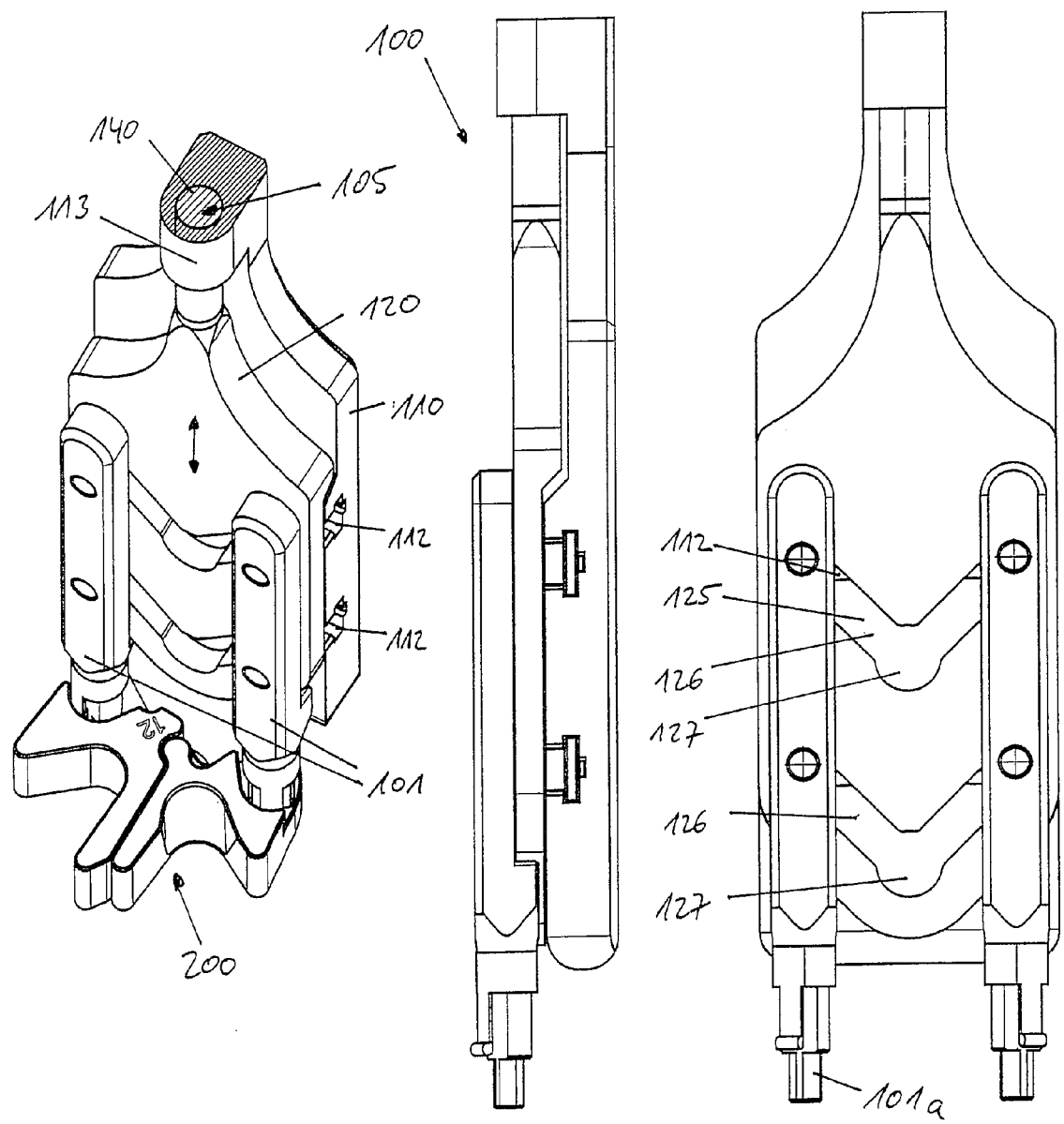
Figure 15:
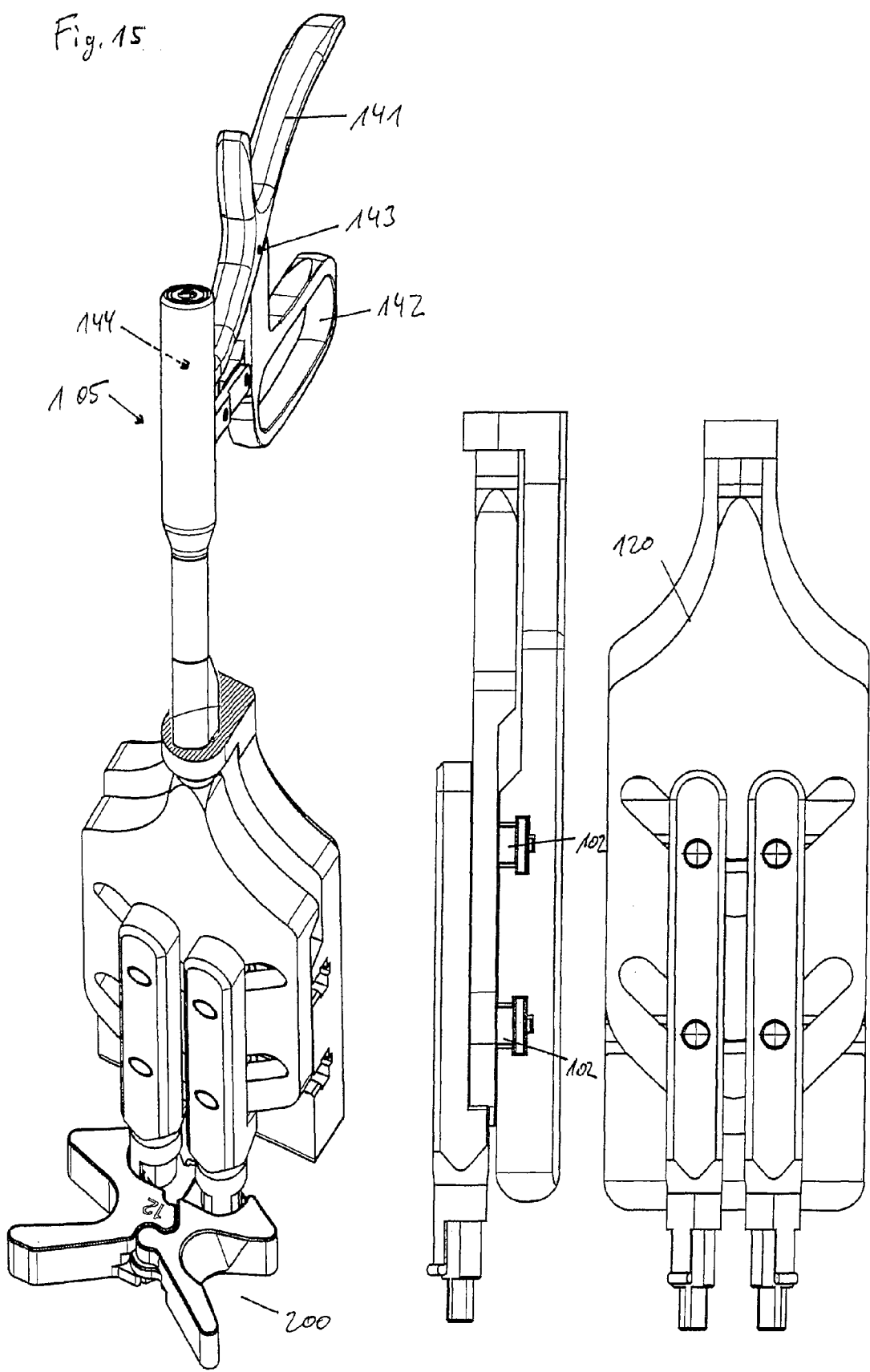

To enable rear projections 9, 10 to be pivoted towards each other, and the two front projections to be opened, the two rear projections display points of application 26 (FIG. 4) in the form of recesses or through-holes that can be engaged by catches of an implantation tool, e.g. according to the practical example in FIGS. 13 to 15. As a result, the essentially V-shaped implant parts can be pivoted relative to each other about the joint located at their vertex.

Joint 6 of the implant displays a first and a second joint element 27, 28 (see FIG. 5, view from the underside), that can be connected to each other in articulated fashion and that can each be developed from the peripheral contours of opposite middle areas 4, 5 of the first and second implant parts. Thus, joint elements 27, 28 only partly project laterally from the peripheral contour of the respective implant part towards the other part, and are partly accommodated within the peripheral contour of the respective part. In this context, a partial area of the joint element can transition into the body of the implant part, and a partial area of the other joint element can be designed as a corresponding receptacle, partly formed in the body. At least one of the joint elements can laterally engage the other implant part. At least one of the joint elements 27 can in this context display a laterally projecting protuberance 29, which is designed as a collar in this instance and which engages an indentation 30 provided in the joint area of the adjacent implant part (cf. FIG. 1). The middle area of the implant can be of comparatively slender design as a result of this. The two joint areas can furthermore form the joint in that they roll on each other in the manner of a rolling bearing, such that the joint is easy to manufacture and sterilize, and deposits in the joint area are avoided. According to the practical example, peripheral contours 29a, 29b, 29c roll on corresponding bearing surfaces of the adjacent implant part on all three levels of the comb-like joint in order to form the joint. The two joint elements 27, 28 can each be designed in one piece with the two associated implant parts, as a result of which the joint is capable of absorbing high forces. Where appropriate, however, they can also be designed as separate parts that are connected to the implant parts.

At least one of the two implant parts (see FIGS. 1-4) can display at least one or more protuberances 51, 52 that laterally engage the other implant part and can be located adjacent to or at a distance from the joint elements, or also transition into them. Both implant parts can also each be provided with at least one or more protuberances that engage the other implant part. In the stabilizing position of the implant, protuberances 51, 52 can, at least in some areas, be located on both sides of a parting or center line 33 of the implant parts. The mutually engaging protuberances can, on the one hand, create the respective joint elements 27, 28. Independently hereof, however, the protuberances, and indentations 54, 55 receiving them, can also (particularly in stabilizing position) form mutually locking areas of the implant parts that absorb forces in certain directions in and/or transverse or perpendicular to the pivoting plane of the implant that act on the connecting area of the two implant parts, especially in stabilizing position, and thus stabilize the implant. In particular, forces acting in a direction perpendicular or transverse or parallel to the longitudinal direction of the vertebral column can also be absorbed by the protuberances in their engaged position. Thus, the lateral outer surfaces 58, 59 of protuberances 51, 52 can be laterally supported on contact surfaces 56, 57 (see FIG. 1) of the other implant part. Thus, for example, contact surfaces arranged at an angle to parting line 33 (see surfaces 32a, 35a) can absorb shear forces acting parallel to parting line 33 or parallel to the direction of insertion of the implant into the intervertebral space. The at least one or more protuberances of the implant part can be received by the other implant part without play and/or in a matching fit, such that, starting from the stabilizing position, the laterally engaging areas of the implant parts preferably do not interlock simply in the event of pivoting towards the insertion position, as is the case with protuberances 51, 52 and indentations 54, 55 with contact surfaces 56, 57. In addition, these protuberances can prevent tilting of the two implant parts relative to each other.

The two implant parts connected to each other in articulated fashion can display interacting securing means, such that, when in assembled state, the two implant parts are secured to each other, in various or at least almost all pivoting positions, except for an assembly position, where appropriate, in non-displaceable fashion and/or in non-tilting fashion in relation to the pivoting plane, such that the implant can be handled as a functional unit, despite simple assembly. Securing to prevent displacement can take place in the pivoting plane or transversely or perpendicularly to it. The assembly position, in which the two implant parts are joined together, can be the insertion position or also another pivoting position, preferably excluding the stabilizing position. For assembly, the two implant parts can (see FIG. 5), for example, be moved towards each other along a path, particularly along an at least essentially linear path (see arrow), in the pivoting plane, until joint elements 27, 28 are fitted together, forming joint 6, where the displacement path can also be arched or curved. Where appropriate, however, assembly can also be performed in a different manner, e.g. by moving the implant parts towards each other in a direction transverse or perpendicular to pivoting plane E, bringing into contact the parts turned out of the pivoting plane in opposite directions, and turning both parts into the pivoting plane, or in some other suitable manner. Displacement can be prevented, particularly transversely to the direction of insertion of the implant into the space between the vertebral processes or in the longitudinal direction of the vertebral column, when the implant parts are pivoted at least slightly out of their assembly position or insertion position towards the stabilizing position. Displacement can be prevented (except in assembly position, where appropriate) in all directions in the pivoting plane of the two implant parts, particularly in stabilizing position, such that the implant parts are connected to each other in force-absorbing fashion in all directions in their pivoting plane.

Given a corresponding design of the two joint areas of the implant parts, the securing means described above can already be provided by said joint areas. Additional securing means or securing means at other points can also be provided, where appropriate, e.g. in the form of mutually engaging protuberances 31, 32 of the two implant parts, which can interact to absorb forces in certain directions, and be located adjacent to the joint.

The above-mentioned securing means can be designed in such a way that the two implant parts engage each other in the manner of a lock in a connecting area that can, in particular, comprise the joint connecting the two implant parts to each other, or also be independent of it. These lock-like securing means can be designed in such a way that they prevent separation of the two implant parts in pivoting plane E (except in their assembly position, where appropriate) and transversely to it.

According to FIG. 5, for example, the connecting means engaging each other in the manner of a lock can be designed in such a way that one of the joint areas 11 displays a lateral, slit-like receiving eye 31, and the other joint area a pivot pin 32 that can be located in the eye and preferably displays a non-round cross-section that can be provided with segment-like corner faces that can lie flat against the joint receptacle or receiving eye. The non-round design results in at least a cross-sectional contraction 32a or also a flat area, such that the pivot pin can be laterally inserted into the receiving eye and is secured to prevent removal following slight rotation in the receptacle. As a result, the two implant parts can be connected to each other by simply sliding them together in the pivoting plane. Even with a different design of the pin, it is possible, where appropriate, to provide a further securing means that at least partly closes the lateral opening of the joint receptacle in order to prevent separation of the implant parts in their insertion position.

Where appropriate, the joint can also be designed in such a way that the two implant parts can be assembled in a direction transverse or perpendicular to the pivoting plane, e.g. in that a pivot pin or an arc-shaped projection is inserted axially into a corresponding receptacle of the other implant part, such that the two implant parts can be pivoted relative to each other. Here, too, projections can be provided that engage each other in the manner of a lock in a certain pivoting position, e.g. the insertion position, and, in another pivoting position, particularly also in the stabilizing position, reach behind each other and are thus secured on each other. A lock of this kind can, for example, be designed in the manner of a bayonet catch.

The implant can furthermore display securing means that secure the two assembled implant parts, at least in their insertion position and/or in their stabilizing position and, where appropriate, also in several or all pivoting positions between these two, to prevent separation or displacement in a direction transverse or perpendicular to the pivoting plane of the implant parts (see FIG. 5). To this end, the joint area can, for example, be provided with a locking pin or similar that passes through both implant parts. In particular, however, these securing means can also be formed in that the two implant parts engage each other in the manner of a comb, at least in some areas, particularly in the area of the joint elements, in order to couple to each other in a manner preventing displacement transverse or perpendicular to the joint plane. To this end, one of the two implant parts can be provided, particularly on its joint element, in the middle area between its upper and lower sides lying parallel to the pivoting plane, with a comb-like projection 36 that is reached over or under, particularly in relation to the pivoting axis, above and below by projections of the adjacent implant part, by the previously described protuberances 51, 52 in this instance (FIG. 1). The same applies to projections 29, 30a, 30b of the joint, which engage each other in comb-like fashion (see FIGS. 1 and 5). The projections engaging each other in comb-like fashion are preferably designed in such a way that they at least couple roughly over the full pivoting angle of the implant parts relative to each other, i.e. between the insertion position and the stabilizing position thereof, in a manner preventing displacement transverse or perpendicular to the pivoting plane. At the same time, these securing means increase the resistance of the implant to tilting of the two implant parts out of the pivoting plane. To this end, the contact surfaces of the two implant parts can also display projections that engage each other in the manner of a comb when in stabilizing position and can be radially separated from the pivoting axis towards the two implant parts, e.g. in the form of protuberances 51, 52 and 36 (see FIGS. 1, 3 and 5). Where appropriate, these areas can also constitute a radial extension of the joint areas engaging each other in the manner of a comb.

The two implant parts can display interacting stops 37, 38 that limit the pivoting angle of the implant parts in their insertion position and/or in their stabilizing position, and that can be designed to be brought into flat contact with each other. In particular, the lateral surfaces of the front and rear projections that face towards each other in the insertion and stabilizing positions of the implant can be designed as stops of this kind, preferably at least essentially over their entire length and/or height.

Furthermore, the implant can display locking means that lock the two implant parts relative to each other in their stabilizing position as a kind of preliminary fixation to prevent pivoting towards their insertion position. The locking means can, in particular, be designed as positive means or snap-fit means, which can display a snap-in tongue 37 and, on the adjacent implant part, an undercut 38, or also as non-positive means, where appropriate. The locking means can be integrally molded on the two implant parts in one piece.

The implant can alternatively or additionally display a lock 40 (see FIGS. 6, 7) that fixes the two implant parts in place relative to each other in their stabilizing position, preferably by means of correspondingly designed positive means 41, 42 in the form of pins 42, provided on a lock body 41, that can engage corresponding receptacles 43 of the implant parts from the upper side of the implant. Receptacles 43 for the lock can be identical to the points of application for the catches of the implantation tool. Lock body 41 can bridge parting line 33 of the implant parts in their stabilizing position. The lock can be designed as a separate component. The lock can be movable up to the implant parts in a direction transverse or perpendicular to their pivoting plane in order to couple to the implant parts in a manner preventing their pivoting. The lock can display retaining means for securing it on the implant parts, e.g. in the form of non-positive and/or positive means, such as snap-in means 45, which reach behind undercuts 46 of the implant parts. The implant parts can display indentations 47, 48 to receive the lock, such that upper side 49 of the lock is preferably at least roughly flush with upper side 50 of the implant parts. The lock or the lock body can cover the top side of securing means 37, 38 for pre-fixing of the implant in its stabilizing position (see FIG. 7).

The invention furthermore relates to a system comprising several implant parts (see FIGS. 9-11), where at least one implant part 60, having a first joint area 60a, and a set of at least two or more implant parts 61, 62, 63, each having a second joint area 61a, are provided, where the first and the second joint area can be connected in articulated fashion, forming joint 6, in order to provide an implant, and where the various implant parts of the set display different designs. Each of the implant parts of the set can be connected in articulated fashion to the at least one first implant part (or also several), forming an implant. The four implant parts shown in FIG. 9 can thus be used to construct three different implants (FIG. 10), where the description regarding FIGS. 1-8 applies accordingly. The designs of the implant parts of the set can, for example, differ as regards their shape and/or dimensions, without being limited to this. For example, the shape of the front and/or rear projections of the implant can differ in the various designs, e.g. the shape of the two front projections from each other or the shape of the two rear projections from each other. The various designs can also display a different width of the middle area located between the front and rear projection, which is located immediately between the vertebral processes. In this way, the implants can display a different distance between the opposite indentations for receiving the vertebral processes (see distance A in FIG. 11), e.g. a distance of 10 mm, 12 mm or 14 mm, where the distance can generally be indicated on the implant (see FIG. 10). Distance A between the indentations on the top side of the implant can be smaller than distance B on the underside of the implant (see FIG. 11). There can in each case also be a difference in the shape and/or size of the indentation located between the front and rear projections for receiving the vertebral processes. The different designs described can also be combined at will. As a result, the implants can be adapted to suit patients of different size and anatomy, and only a relatively small number of different implants is needed to cover a wide range of applications in terms of differently shaped or dimensioned vertebral columns. The preceding description applies to the individual implant parts in all other respects. Joint areas 61a of the set of implant parts 61, 62, 63 can be of identical design, although this is not always necessary as long as the joint areas can be connected to form an implant. Additionally or independently hereof, one or more of the following features can be of identical design on some or all of the implant parts of the set: the contact areas 61b of the implant parts lying opposite first implant part 60; the protuberances projecting towards the opposite implant part; the locking means for fixing (pre-fixing) the implants in their stabilizing position; the lock receptacle for the lock; the means for securing the implant parts to each other, particularly those for preventing displacement in the axial direction and/or in the pivoting plane; the areas of the engaging comb structures located on these implant parts, etc. These are generally functional elements that interact with functional elements of the adjacent implant part. It goes without saying that an identical design of all the above-mentioned features is not always absolutely necessary.

Figure 12A:
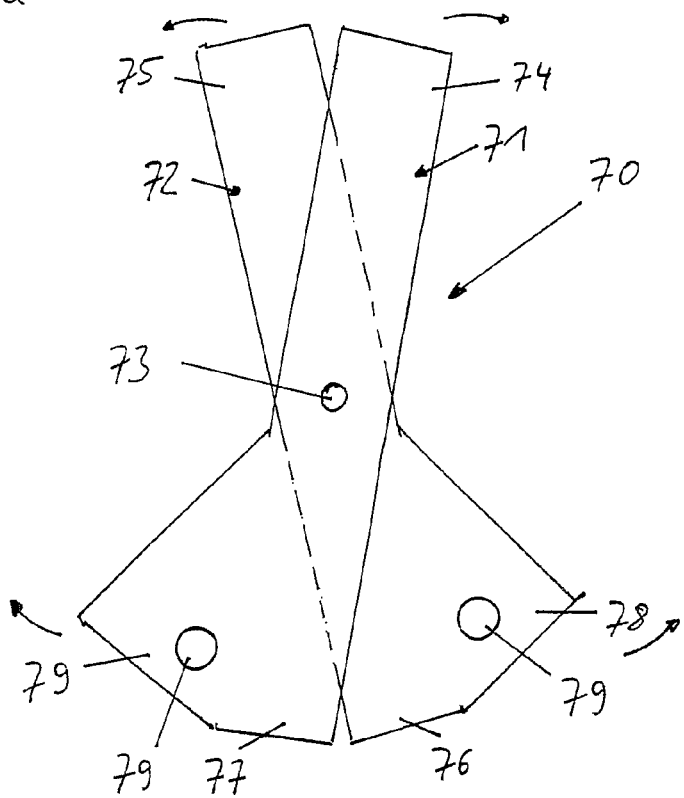
Figure 12B:
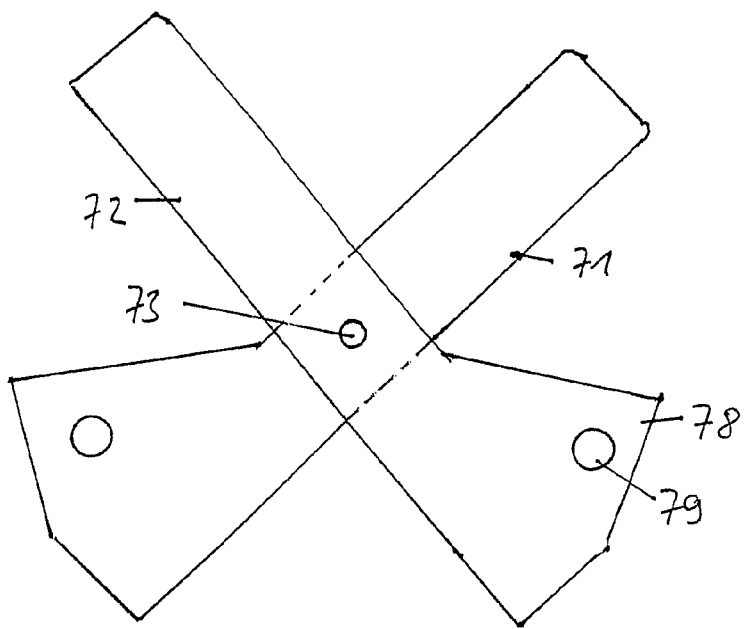

FIG. 12 shows a highly schematic representation of a further embodiment of an implant 70 according to the invention, in which the two implant parts 71, 72 display a joint 73 in their middle area that connects them to each other in the manner of scissors. The corresponding joint elements of the two implant parts can be connected to each other in detachable or permanent fashion, e.g. in accordance with the joints elements as per FIGS. 1 to 8. In the insertion position shown in FIG. 12a, both the two front projections 74, 75 and the two rear projections 76, 77 are thus adjacent to or in contact with each other. Where appropriate, projections 74 to 77 can also overlap almost completely in their insertion position. By spreading open the two rear projections and pivoting the two at least essentially rigid implant parts relative to each other, the two front projections also pivot due to coupled motion, moving apart from each other and spreading open the implant. It goes without saying that the sides of projections 74 to 77 lying opposite the vertebral processes can have a shape adapted to the latter. One or both of rear projections 76, 77 can be provided with a plateau-like wider area, which can in each case be located on the side facing away from the opposite projection of the other implant part, as illustrated in FIG. 12b. Where appropriate, however, one or both of the plateau-like wider areas can also be located on the side facing towards the adjacent projection. Here, too, the preferably plateau-like wider areas 78 can be equipped with further functional means, e.g. with points of application 79 for the catches of an implantation tool according to FIGS. 14 to 16. A locking means, which can be designed in accordance with that in FIGS. 1 to 8, can furthermore again be provided here to fix the implant parts in their stabilizing position. The implant parts can display corresponding receptacles to this end. If the implant is designed in such a way that the two plateau-like wider areas overlap each other when the implant is in its insertion position, one of the projections can, where appropriate, display a laterally open, slit-like recess to allow application of the catches of the implantation tool in order to move the implant into its stabilizing position. If nothing different results, the description relating to the practical example according to FIGS. 1 to 8 applies accordingly here.

FIG. 13 shows a schematic representation of a modification of an implant 80 pursuant to the practical example according to FIGS. 1 to 8, where reference is made in full to the content of the description relating to this practical example, insofar as nothing different results. The implant is in its insertion position. The two implant parts 81, 82 are of essentially V-shaped design and display joint elements 83, 84, e.g. pivot pins, that are, however, connected to each other by an intermediate piece 85. Areas 86 of the intermediate piece overlapping the two implant parts can, for example, be located in a recess located on the underside of the implant and preferably lie essentially flush with the underside of the implant, or be received by pocket-like, laterally open recesses of the implant parts, or be connected to the latter in articulated fashion in some other suitable way. Implant parts 81, 82 are thus not directly connected to each other in articulated fashion, and this can apply generally in the framework of the invention. In all other respects, the handling corresponds to that of the practical example according to FIGS. 1-8.

Figure 16:
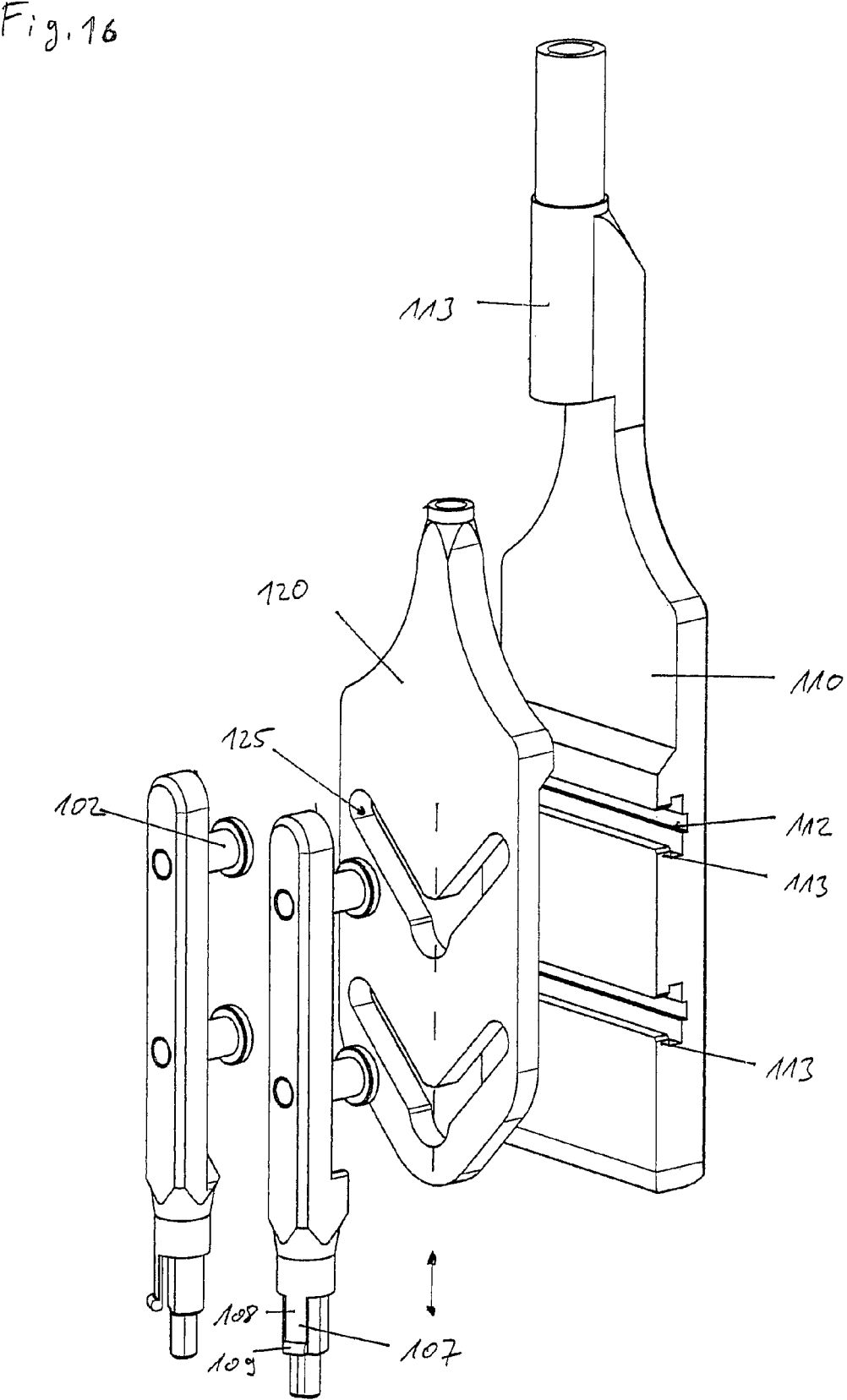

FIGS. 14 to 16 show an embodiment of a tool according to the invention for implanting an implant according to the invention. Tool 100 displays two catches 101 that can be displaced relative to each other so that, when in an insertion position (see FIG. 14), they can couple to implant 200, which is in its insertion position. The catches are laterally spaced apart from each other in this position. In this context, catches 101 can be moved by suitable actuating means 105 into an implantation position (see FIG. 15) in which implant 200 is in its stabilizing position. In this position, catches 101 are a smaller distance apart than in the insertion position (see FIG. 15), or at least roughly in lateral contact with each other. It goes without saying that the converse applies accordingly in the case of an implant according to FIG. 12.

On a holding structure 110, formed by a plane base plate in this case, the tool displays positive guides 112 for the catches, preferably at least roughly parallel positive guides, which are engaged by the catches, each with two retaining elements 102. Catches 101 can be displaced parallel to each other, preferably maintaining their distance from the principal center plane of the implant, where their displacement can take place in one plane. To move catches 101, an actuator device 120 is provided, which is movable relative to positive guides 112 and, when moved by means of actuator elements 125, acts indirectly or directly on the catches. Actuator device 120 can be of dimensionally stable design. According to the practical example, the device is designed as an actuator plate that displays high dimensional stability and is easy to manufacture, although it is also possible to use a different suitable design that preferably displays no parts moving relative to each other and/or can be designed in one piece. The catches can thus be displaced in the principal plane of the actuator device, changing the distance between them, where the catches can remain parallel to each other. A suitable guide can be provided for this purpose, to which end the catches can each display two retaining elements 102, spaced apart in the longitudinal direction.

Actuator elements 125 are provided in the form of two guides 126 that are located in a plane and include an angle relative to each other, where the two guides are arranged parallel to each other. The two vertices 127 of the guides lie on a line parallel to the catches. Using actuating means 105, actuator device 120 can be displaced parallel to the line connecting the vertices, such that displacement of the actuator plate in the direction of the arrow according to FIG. 14 moves it into its position according to FIG. 15, as a result of which the catches are displaced towards each other. In this way, the implant can be moved into its stabilizing position, as shown in FIG. 15.

In this context, vertices 127 point downwards or towards the implant. If displacement of the actuator device in the same direction is to move the catches apart (instead of reducing the distance), e.g. in the case of an implant according to FIG. 14, the guides can be rotated through 180° and arranged with their vertices 127 pointing upwards.

The actuator elements designed as guides 126 each intersect positive guides 112 of holding structure 110 at two points, i.e. at the level of retaining elements 102 of the catches, such that both catches can be displaced relative to the implant by coupled motion when the actuator device is displaced relative to positive guides 112, changing the distance of the actuator device from the implant. The retaining elements of the catches then move relative to both positive guides 112 and the actuator elements, and can be displaceable in both. Retaining elements 102, which reach through guides 126 of the actuator device, are retained in captive manner on holding structure 110, to which end the retaining elements reach behind undercuts 113 of the positive guides. To enable securing of the retaining elements, the guides of the actuator plate display at least an area with a wider cross-section 128 than permits insertion of the retaining areas of the catches. In this instance, the area with a wider cross-section is located in the middle area of the guides. In this context, guides 126 run at an angle to the direction of movement of the actuator plate. The areas of guides 126 assigned to the respective catch (i.e. the guide areas extending from the vertices in each case) are of linear design in this instance, although a curved design is also possible.

Catches 101 can be moved towards the implant in a direction perpendicular to the pivoting plane of the implant in order to couple to it by means of bolt-like projections 101a. The catches can generally display retaining elements 107 for temporary securing of catches 101 on the implant, e.g. in order to position implant 100 on the vertebral column or insert it into the space between vertebral processes. The retaining elements can be coupled to the implant by applying tensile force or pressure transversely or perpendicularly to the pivoting plane of the implant. To this end, the retaining elements can display snap-in means, e.g. in the form of resilient tongues 108 with snap-in projections 109, that can be released by applying tensile force.

Actuating means 105 for the actuator device can display means 140 that preferably simultaneously transmit tensile and pressure forces, such as a set of rods that is designed in such a way that, following axial movement transversely or at least essentially perpendicularly to the pivoting plane of the implant parts, resulting in a change in the distance from the pivoting plane, it acts on the catches to move them from their coupling position into their implantation position. The displaceable set of rods can be guided in rod guide 113 on holding structure 110.

The actuating means can, as illustrated in FIG. 15, be displaceable by means of a pivoting lever 141 in order to bring about displacement of the actuator device or actuator plate. Pivoting lever 141 can be located on a handle 142 in pivoting fashion by means of a joint 143, and coupled to the set of rods by a further joint 144 a distance away. The actuating means can thus display a handle for one-hand actuation of the tool, where said actuating means are designed in such a way that, when the tool is actuated, the handle is located in an immovable position relative to the positive guide of the catches and/or the vertebral column of the patient. To this end, an actuator device, e.g. an actuator plate, can be provided that couples onto the catches and can be moved relative to the positive guides of the catches, which make it possible to change the distance between the catches. The positive guides of the catches can be designed to be immovable relative to the handle. This greatly facilitates application of the implant.

Actuating means 105 for transmitting tensile and/or pressure forces can be of elongated design, to which end an elongated transmission device can be provided, such as a set of rods, a traction cord arrangement or similar. The tool can be designed in such a way that, in the actuating position of the tool, the actuating means, particularly when designed as an elongated actuating means, is located or oriented transversely, particularly perpendicularly, to the longitudinal direction of the vertebral column of the patient to be treated and/or transversely, particularly perpendicularly, to the principal plane of the patient, and the actuating means can be moved in this direction in order to open or close the implant by means of the tool. The principal plane of the patient is the plane between the two shoulders and the pelvis. The principal plane of the patient can correspond to the principal plane of the implant. Thus, when the tool is actuated, the actuating means or trans-mission device can be moved transversely or perpendicularly to the vertebral column and/or transversely or perpendicularly to the principal plane of the patient. Movement parallel to the longitudinal direction of the vertebral column can be omitted.

It goes without saying that alternative embodiments of the tool are also conceivable. For example, movement of the catches towards each other can be brought about by traction mechanisms, such as a traction cord, in which context separation of the catches to move them into their starting position can be accomplished by suitable spring elements. Preference is, however, given to return movement by the actuating means transmitting tensile and pressure forces. It furthermore goes without saying that, where appropriate, the actuator plate or suitable actuating means can bring about movement of the catches not only by longitudinal displacement perpendicular to the pivoting plane of the implant, but also, for example, by an actuator plate mounted in rotating fashion with arc-shaped guides as actuator elements that move the catches together or apart.

Where appropriate, the linear positive guide for the catches can furthermore also be replaced by a non-linear positive guide, e.g. an arc-shaped positive guide. Where appropriate, the positive guide can furthermore not be located in a plane that is preferably perpendicular to the pivoting plane of the implant, as illustrated in the practical examples; where appropriate, the positive guide can also be of arc-shaped design in the pivoting plane of the implant.

What is claimed is:

1. An implant locatable between adjacent vertebral processes of vertebrae of a vertebral column to separate adjacent vertebrae from each other, the implant comprising:
at least two implant parts, wherein the two implant parts are connectable and pivotable by a joint, and wherein the two implant parts are pivotable relative to one another in a pivoting plane from an insertion position to a stabilizing position between adjacent vertebrae,
each of the two implant parts comprising a front projection and a rear projection between which the joint is located, wherein, in the insertion position, the two front projections are adjacent each other to be insertable into a space between the adjacent vertebrae, and wherein, in the stabilizing position, the two front projections are locatable on one side of the vertebral column laterally adjacent to the adjacent vertebrae and the two rear projections are locatable on an opposite side of the vertebral column laterally adjacent to the adjacent vertebrae, and wherein the two implant parts are pivotable from the insertion position to the stabilizing position by applying a force to the two rear projections in a pivoting direction such that the front projections spread open from one another and the rear projections close towards one another,
wherein each of the two implant parts have an essentially V-shaped design having a middle vertex area, wherein the two vertex areas are arranged facing each other when the two implant parts are connected,
wherein each of the two implant parts have joint areas forming the joint which are integrated in the respective implant parts and provide bearing surfaces which roll on each other,
wherein one joint area comprises a laterally projecting protuberance and the other joint area comprises an indentation receiving the protuberance,
wherein the two implant parts are connectable by rotation in the pivoting plane and, when connected, are engaged with securing means which inhibit separation of the two implant parts in the pivoting plane except in an assembly position, wherein the two implant parts are connectable in the pivoting plane by a positioning of the two implant parts in the assembly position wherein a pivot pin of one of the implants is aligned with a receiving eye of the other one of the implants such that the pivot pin is laterally insertable into a lateral opening in the receiving eye by a lateral movement of at least one of the implants towards the other implant in the pivoting plane; and wherein, once the pivot pin is in the receiving eye, the two implant parts are inhibited from lateral separation in the pivoting plane by engagement of the pivot pin and receiving eye except in the assembly position.

2. The implant according to claim 1, wherein the joint is located in the middle vertex area of the two implant parts and connects the two implant parts to each other in a scissor-like manner.

3. The implant according to claim 1, wherein the two implant parts, when connected, are secured to prevent displacement relative to each other transverse to the pivoting plane, at least in the stabilizing position.

4. The implant according to claim 1, wherein the two implant parts include interacting stops that limit a pivoting angle of the two implant parts in the insertion position, or in the stabilizing position, or in both positions.

5. The implant according to claim 1, further comprising locking means that lock the two implant parts relative to each other in the stabilizing position to prevent pivoting towards the insertion position.

6. The implant according to claim 1, wherein the implant includes a lock that fixes the two implant parts in place relative to each other when in the stabilizing position.

7. The implant according to claim 1, wherein a separate locking element bridges the two implant parts and includes positive means for positive coupling on the two implant parts, fixing them in place relative to each other.

8. The implant according to claim 1, wherein the two implant parts include points of application for coupling to an implantation tool, where the points of application are on a line lying eccentrically to the pivoting axis of the two implant parts.

9. The implant according to claim 1, further comprising a third implant part in addition to the two implant parts wherein the third implant part is exchangeable one of the two implant parts to change at least one of a shape and/or dimension of the implant.

10. An implant locatable between adjacent vertebral processes of the vertebrae of a vertebral column to separate adjacent vertebrae from each other, the implant comprising:

at least two implant parts, wherein the two implant parts are connectable and pivotable by a joint, and wherein the two implant parts are pivotable relative to one another in a pivoting plane from an insertion position to a stabilizing position between adjacent vertebrae, each of the two implant parts comprising a front projection and a rear projection between which the joint is located, wherein, in the insertion position, the two front projections are adjacent each other to be insertable into a space between the adjacent vertebrae, and wherein, in the stabilizing position, the two front projections are locatable on one side of the vertebral column laterally adjacent to the adjacent vertebrae and the two rear projections are locatable on an opposite side of the vertebral column laterally adjacent to the adjacent vertebrae, and wherein the two implant parts are pivotable from the insertion position to the stabilizing position by applying a force to the two rear projections in a pivoting direction such that the front projections spread open from one another and the rear projections close towards one another, wherein each of the two implant parts have an essentially V-shaped design, having a middle vertex area, wherein the two vertex areas are arranged facing each other when the two implant parts are connected, wherein both implant parts are arranged side-to-side, and wherein the two implant parts are connectable by rotation in the pivoting plane and, when connected, are engaged with securing means which inhibit separation of the two implant parts in the pivoting plane except in an assembly position, wherein the two implant parts are connectable in the pivoting plane by a positioning of the two implant parts in the assembly position wherein a pivot pin of one of the implants is aligned with a receiving eye of the other one of the implants such that the pivot pin is laterally insertable into a lateral opening in the receiving eye by a lateral movement of at least one of the implants towards the other implant in the pivoting plane; and wherein, once the pivot pin is in the receiving eye, the two implant parts are inhibited from lateral separation in the pivoting plane by engagement of the pivot pin and receiving eye except in the assembly position.

11. An implant locatable between adjacent vertebral processes of the vertebrae of a vertebral column in order to separate adjacent vertebrae from each other, the implant comprising:

at least two implant parts, wherein the two implant parts are connectable and pivotable by a joint, and wherein the two implant parts are pivotable relative to one another in a pivoting plane from an insertion position to a stabilizing position between adjacent vertebrae, each of the two implant parts comprising a front projection and a rear projection between which the joint is located, wherein, in the insertion position, the two front projections are adjacent each other to be insertable into a space between the adjacent vertebrae, and wherein, in the stabilizing position, the two front projections are locatable on one side of the vertebral column laterally adjacent to the adjacent vertebrae and the two rear projections are locatable on an opposite side of the vertebral column laterally adjacent to the adjacent vertebrae, and wherein the two implant parts are pivotable from the insertion position to the stabilizing position by applying a force to the two rear projections in a pivoting direction such that the front projections spread open from one another and the rear projections close towards one another, wherein each of the two implant parts have an essentially V-shaped design having a middle vertex area, wherein the two vertex areas are arranged facing each other when the two implant parts are connected, wherein the implant includes a lock that fixes the two implant parts in place relative to each other when in the stabilizing position, wherein the lock comprises a separate locking element that bridges the two implant parts and includes positive means for positive coupling on the two implant parts, fixing them in place relative to each other, wherein the locking element comprises a longitudinal axis and in a locking position the longitudinal axis of the locking element is arranged in the pivoting plane, and wherein the two implant parts are connectable by rotation in the pivoting plane and, when connected, are engaged with securing means which inhibit separation of the two implant parts in the pivoting plane except in an assembly position, wherein the two implant parts are connectable in the pivoting plane by a positioning of the two implant parts in the assembly position wherein a pivot pin of one of the implants is aligned with a receiving eye of the other one of the implants such that the pivot pin is laterally insertable into a lateral opening in the receiving eye by a lateral movement of at least one of the implants towards the other implant in the pivoting plane; and wherein, once the pivot pin is in the receiving eye, the two implant parts are inhibited from lateral separation in the pivoting plane by engagement of the pivot pin and receiving eye except in the assembly position.

12. An implant locatable between adjacent vertebral processes of the vertebrae of a vertebral column in order to separate adjacent vertebrae from each other, the implant comprising:

at least two implant parts, wherein the two implant parts are connectable and pivotable by a joint, and wherein the two implant parts are pivotable relative to one another in a pivoting plane from an insertion position to a stabilizing position between adjacent vertebrae, each of the two implant parts comprising a front projection and a rear projection between which the joint is located, wherein, in the insertion position, the two front projections are adjacent each other to be insertable into a space between the adjacent vertebrae, and wherein, in the stabilizing position, the two front projections are locatable on one side of the vertebral column laterally adjacent to the adjacent vertebrae and the two rear projections are locatable on an opposite side of the vertebral column laterally adjacent to the adjacent vertebrae, and wherein the two implant parts are pivotable from the insertion position to the stabilizing position by applying a force to the two rear projections in a pivoting direction such that the front projections spread open from one another and the rear projections close towards one another, wherein each of the two implant parts have an essentially V-shaped design having a middle vertex area, wherein the two vertex areas are arranged facing each other when the two implant parts are connected, wherein the implant includes a lock that fixes the two implant parts in place relative to each other when in the stabilizing position, wherein the lock comprises a separate locking element that bridges the two implant parts and includes positive means for positive coupling on the two implant parts, fixing them in place relative to each other, wherein the locking element comprises a body and spaced apart pins and at least one of the projections of each of the implant parts is provided with a receptacle adapted to receive the pins for locking the implant, and wherein the two implant parts connectable by rotation in the pivoting plane and, when connected, are engaged with securing means which inhibit separation of the two implant parts in the pivoting plane except in an assembly position.

13. An implant locatable between adjacent vertebral processes of the vertebrae of a vertebral column in order to separate adjacent vertebrae from each other, the implant comprising:

at least two implant parts, wherein the two implant parts are connectable and pivotable by a joint, and wherein the two implant parts are pivotable relative to one another in a pivoting plane from an insertion position to a stabilizing position between adjacent vertebrae, each of the two implant parts comprising a front projection and a rear projection between which the joint is located, wherein, in the insertion position, the two front projections are adjacent each other to be insertable into a space between the adjacent vertebrae, and wherein, in the stabilizing position, the two front projections are locatable on one side of the vertebral column laterally adjacent to the adjacent vertebrae and the two rear projections are locatable on an opposite side of the vertebral column laterally adjacent to the adjacent vertebrae, and wherein the two implant parts are pivotable from the insertion position to the stabilizing position by applying a force to the two rear projections in a pivoting direction such that the front projections spread open from one another and the rear projections close towards one another, wherein each of the two implant parts have an essentially V-shaped design having a middle vertex area, wherein the two vertex areas are arranged facing each other when the two implant parts are connected, wherein the implant includes a lock that fixes the two implant parts in place relative to each other when in the stabilizing position, wherein the lock comprises a separate locking element that bridges the two implant parts and act on the projections of the implant parts to lock the implant parts with each other, and wherein the two implant parts are connectable by rotation in the pivoting plane and, when connected, are engaged with securing means which inhibit separation of the two implant parts in the pivoting plane except in an assembly position, wherein the two implant parts are connectable in the pivoting plane by a positioning of the two implant parts in the assembly position wherein a pivot pin of one of the implants is aligned with a receiving eye of the other one of the implants such that the pivot pin is laterally insertable into a lateral opening in the receiving eye by a lateral movement of at least one of the implants towards the other im lant in the pivoting plane; and wherein, once the pivot pin is in the receiving eye, the two implant parts are inhibited from lateral separation in the pivoting plane by engagement of the pivot pin and receiving eye except in the assembly position.

14. An implant locatable between adjacent vertebral processes of vertebrae of a vertebral column to separate adjacent vertebrae from each other, the implant comprising:

at least two implant parts, wherein the two implant parts are connectable and pivotable by a joint, and wherein the two implant parts are pivotable relative to one another in a pivoting plane from an insertion position to a stabilizing position between adjacent vertebrae, each of the two implant parts comprising a front projection and a rear projection between which the joint is located, wherein, in the insertion position, the two front projections are adjacent each other to be insertable into a space between the adjacent vertebrae, and wherein, in the stabilizing position, the two front projections are locatable on one side of the vertebral column laterally adjacent to the adjacent vertebrae and the two rear projections are locatable on an opposite side of the vertebral column laterally adjacent to the adjacent vertebrae, and wherein the two implant parts are pivotable from the insertion position to the stabilizing position by applying a force to the two rear projections in a pivoting direction such that the front projections spread open from one another and the rear projections close towards one another, wherein each of the two implant parts have an essentially V-shaped design having a middle vertex area, wherein the two vertex areas are arranged facing each other, wherein the two implant parts are connectable in the pivoting plane by a positioning of the two implant parts in an assembly position wherein a pivot pin of one of the implants is aligned with a receiving eye of the other one of the implants such that the pivot pin is laterally insertable into a lateral opening in the receiving eye by a lateral movement of at least one of the implants towards the other implant in the pivoting plane; and wherein, once the pivot pin is in the receiving eye, the two implant parts are inhibited from lateral separation in the pivoting plane by engagement of the pivot pin and receiving eye except in the assembly position.

* * * * *

UNITED STATES PATENT AND TRADEMARK OFFICE
CERTIFICATE OF CORRECTION

PATENT NO.       : 8,439,950 B2
APPLICATION NO.  : 12/263890
DATED            : May 14, 2013
INVENTOR(S)      : Zentes et al.

Page 1 of 1

It is certified that error appears in the above-identified patent and that said Letters Patent is hereby corrected as shown below:

In the Claims:

In column 20, line 42, delete "im lant" and insert -- implant --, therefor.

Signed and Sealed this
Seventeenth Day of September, 2013

Teresa Stanek Rea
*Deputy Director of the United States Patent and Trademark Office*